US 6,674,522 B2
Jan. 6, 2004

(54) EFFICIENT PHASE DEFECT DETECTION SYSTEM AND METHOD

(75) Inventors: Matthias C. Krantz, Aptos, CA (US); Mark Joseph Wihl, Tracy, CA (US); Stanley E. Stokowski, Danville, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 26 days.

(21) Appl. No.: 09/849,614

(22) Filed: May 4, 2001

(65) Prior Publication Data

US 2002/0171825 A1 Nov. 21, 2002

(51) Int. Cl.$^7$ .............................................. G01N 21/88
(52) U.S. Cl. ............................ 356/237.1; 356/237.5; 356/239.3
(58) Field of Search .......................... 356/237.1, 239.1, 356/239.2, 239.3, 239.7, 239.8, 237.2, 237.3, 237.4, 237.5, 237.6

(56) References Cited

U.S. PATENT DOCUMENTS

| | | | |
|---|---|---|---|
| 3,902,805 A | * | 9/1975 | Redner .......................... 356/33 |
| 4,247,203 A | | 1/1981 | Levy et al. |
| 4,579,455 A | | 4/1986 | Levy et al. |
| 5,076,696 A | * | 12/1991 | Cohn et al. .................. 356/369 |
| 5,439,767 A | | 8/1995 | Yamashita |
| 5,563,702 A | | 10/1996 | Emery et al. |
| 5,572,598 A | | 11/1996 | Wihl et al. |
| 5,631,721 A | | 5/1997 | Stanton et al. |
| 5,684,566 A | | 11/1997 | Stanton |
| 5,801,874 A | | 9/1998 | Montgomery et al. |
| 5,801,954 A | | 9/1998 | Le et al. |
| 6,052,478 A | | 4/2000 | Wihl et al. |
| 6,067,375 A | | 5/2000 | Tsudaka |
| 6,134,011 A | | 10/2000 | Klein et al. |
| 6,268,093 B1 | | 7/2001 | Kenan et al. |
| 6,307,627 B1 | * | 10/2001 | Vurens ........................ 356/369 |

OTHER PUBLICATIONS

"Transferring Phase–Shifting Mask Technology into Mainstream Manufacturing," D. Van Den Broeke, *www.semiconductorfabtech.com/features/lithography/articles/body5.225.php3*, 1982, pp.1–7.

"Fourier Imaging of Phase Information in Scanning and Conventional Optical Microscopes," C.J.R. Sheppard et al., *Philosophical Transactions of the Royal Society of London, A. Mathematical and Physical Sciences*, vol. 295, No. 1415, Feb. 7, 1980, pp. 513–536.

(List continued on next page.)

*Primary Examiner*—Richard A. Rosenberger
(74) *Attorney, Agent, or Firm*—Parsons Hsue & de Runtz LLP

(57) ABSTRACT

The ability to inspect photomasks for errors or defects in phase-shifters is greatly enhanced using optical techniques based on multiple modified radiation collection techniques. In particular, the apparatus and methods of the invention allows for errors in phase-shifters to be more accurately detected, even in the presence of regular amplitude objects such as grid lines. In one embodiment, the intensities of two slightly defocused images of phase objects corresponding to the same photomask location are compared. In a second embodiment, radiation having two Zernike point spread functions is used to obtain two slightly different phase sensitive images. Data collected and analyzed using this method provides much greater sensitivity to phase objects and errors in phase objects than prior art inspection systems. Embodiments include both scanning-type and projector-type optical architectures and may utilize radiation transmitted or reflected by a sample.

88 Claims, 18 Drawing Sheets

OTHER PUBLICATIONS

"Noninterferometric quantitative phase imaging with soft xrays," B. E. Allman et al., *J. Opt. Soc. Am*, vol. 17, No. 10, Oct. 2000, pp. 1732–1743.

"Image processing using additional statistical information about the object," P. Schiske, *Image Processing and Computer–Aided Design in Electron Optics*, P.W. Hawkes, ed. (Academic, New York, 1973), pp. 82–90.

"Phase retrieval through focus variation for ultra–resolution in field–emission transmission microscopy," W. Coene et al., *PHys. Rev. lett.*, 69, Dec. 28, 1992, pp. 3743–3746.

Hamilton et al., "Differential Phase Contrast in Scanning Optical Microscopy," *Journal of Microscopy*, vol. 33, Jan., 1984, pp. 27–39.

* cited by examiner

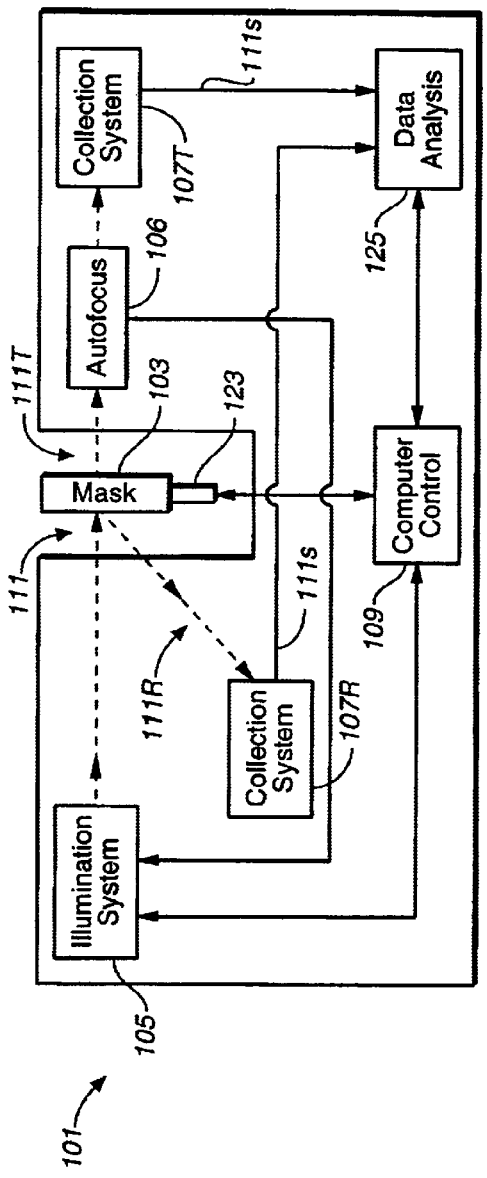
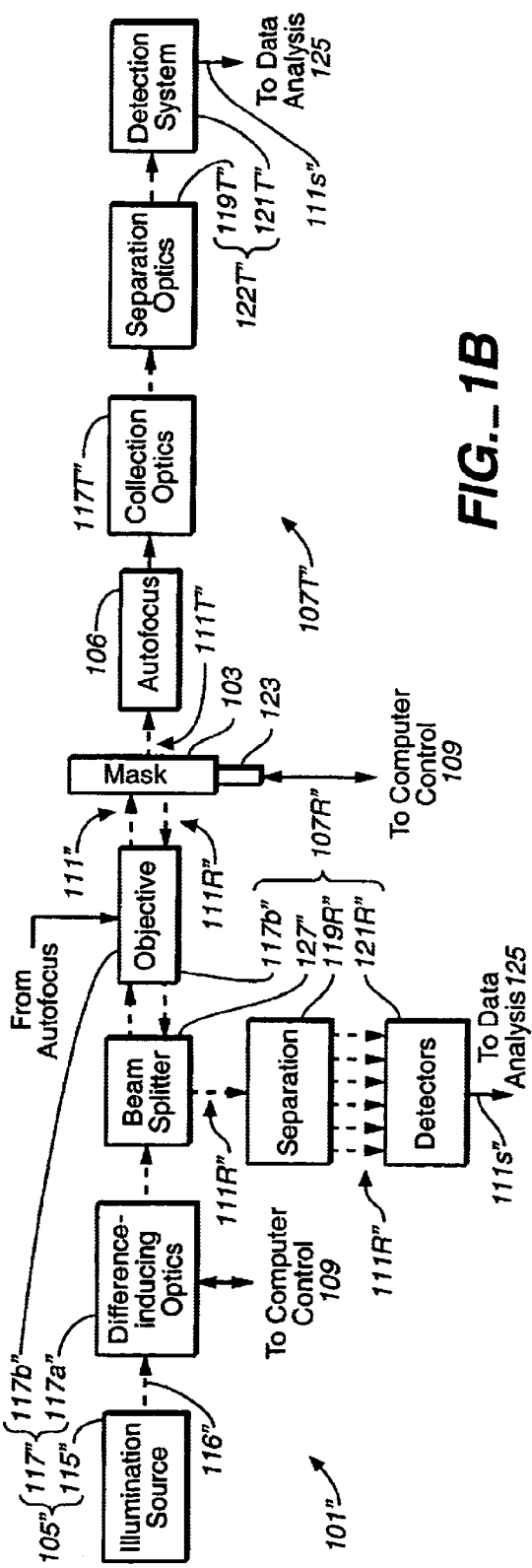
FIG._1A
FIG._1B

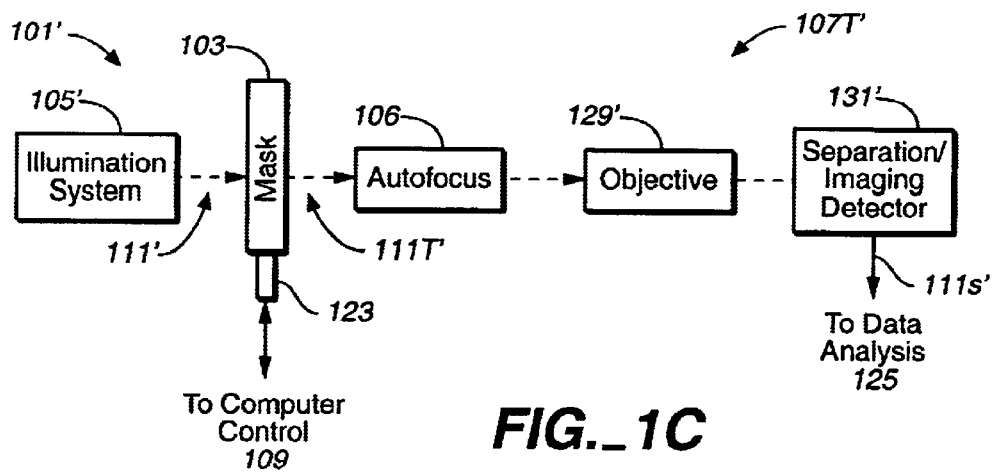
FIG._1C
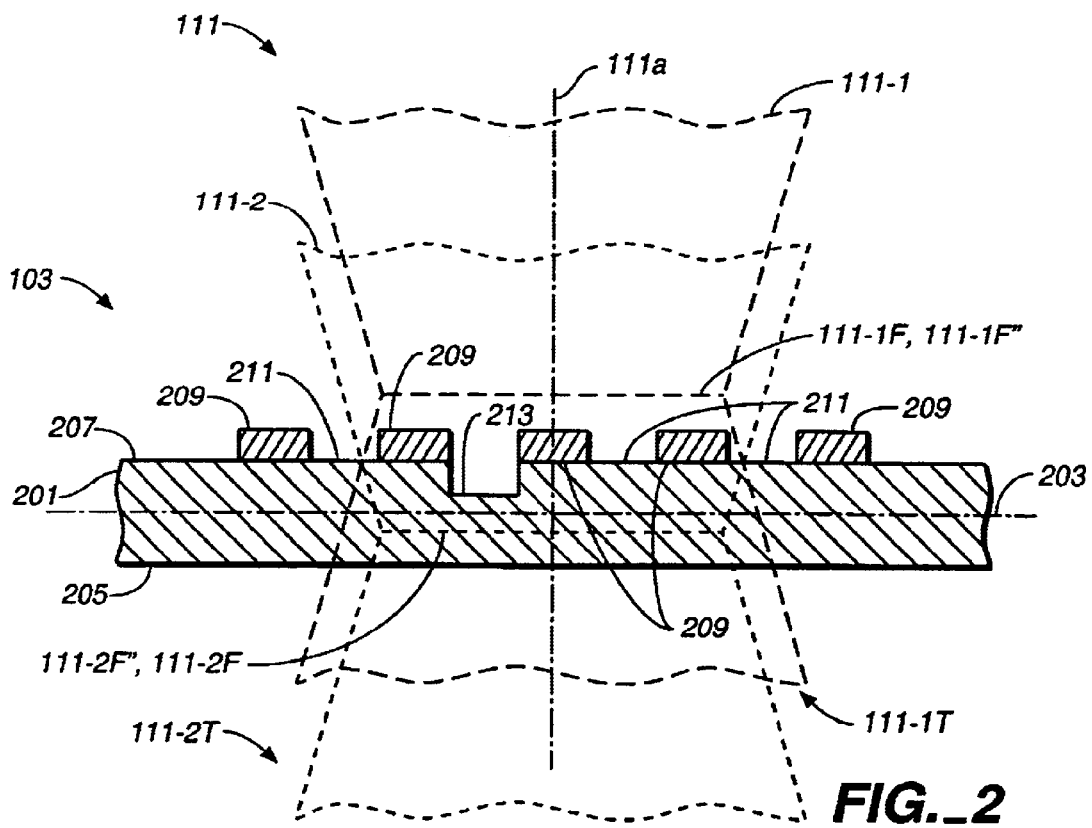
FIG._2

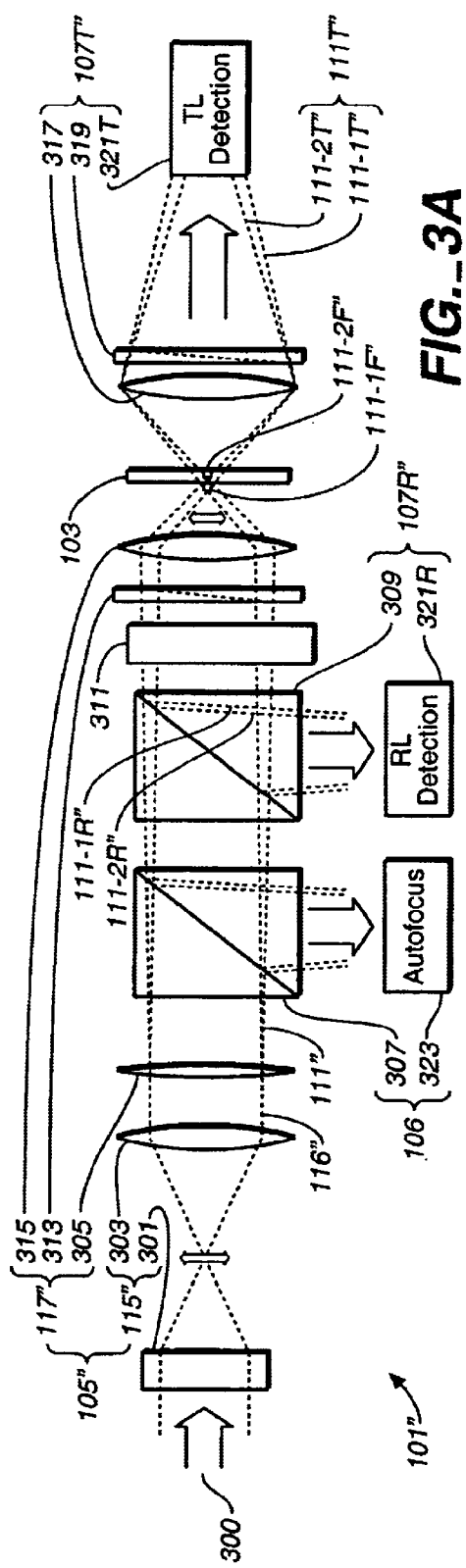
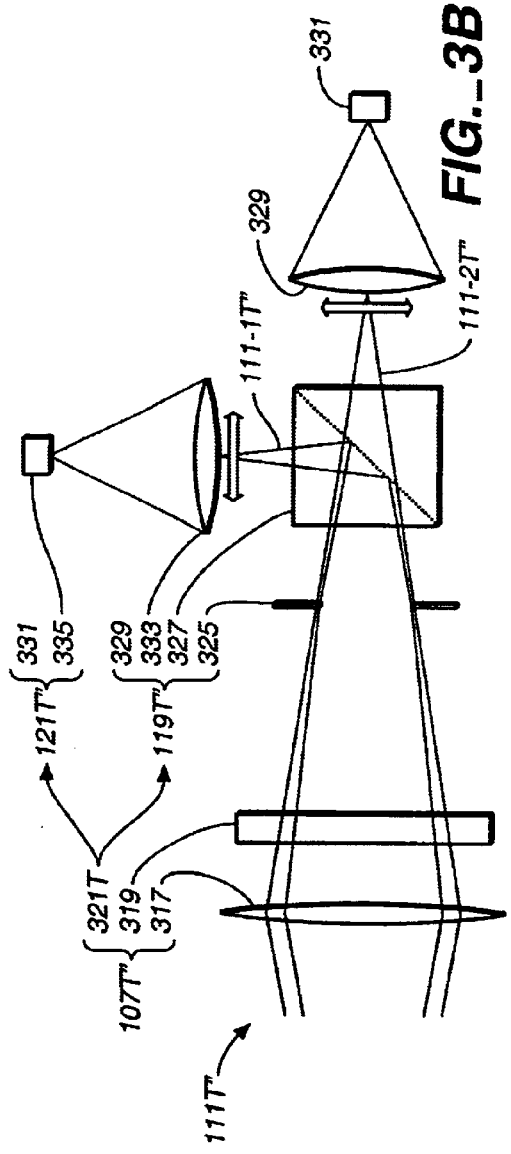
FIG._3A
FIG._3B

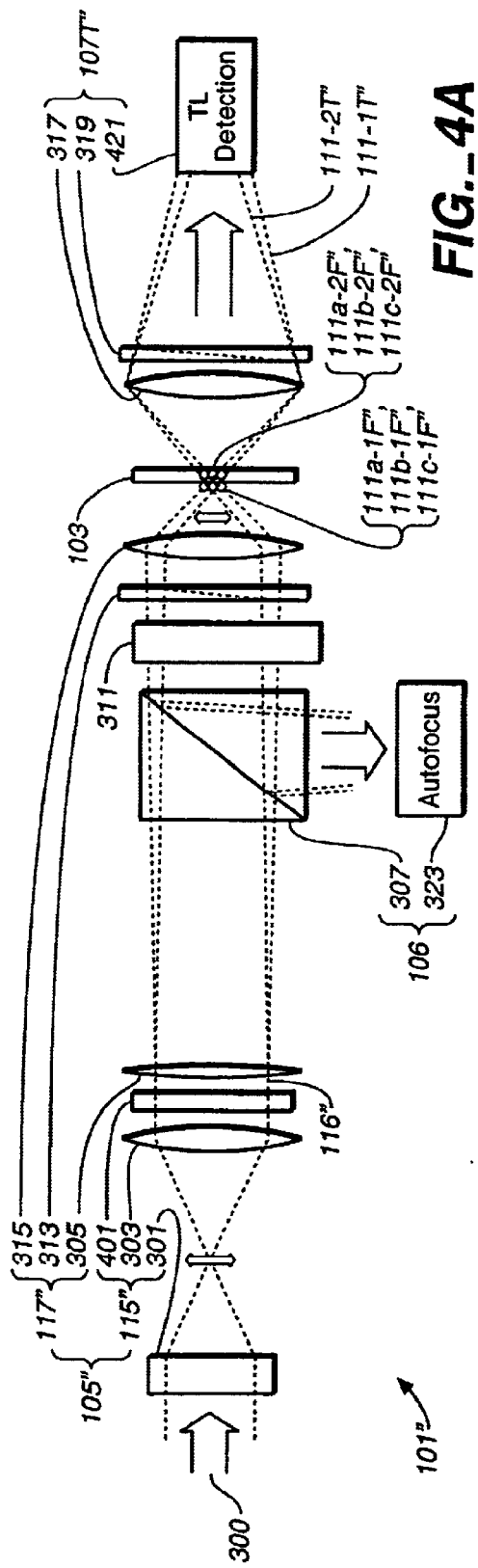
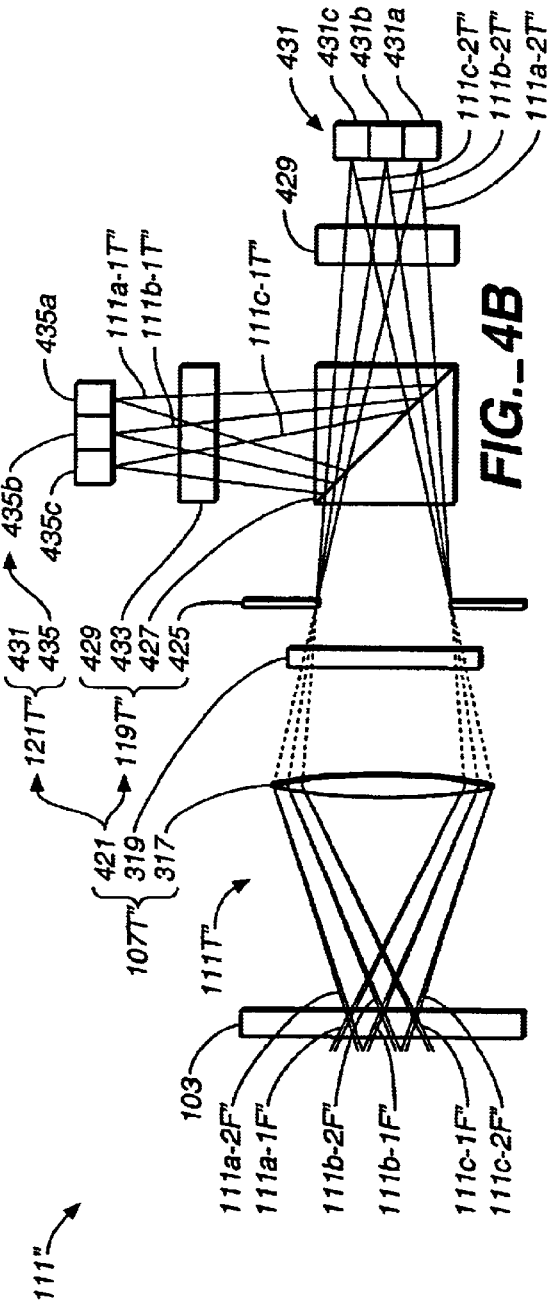

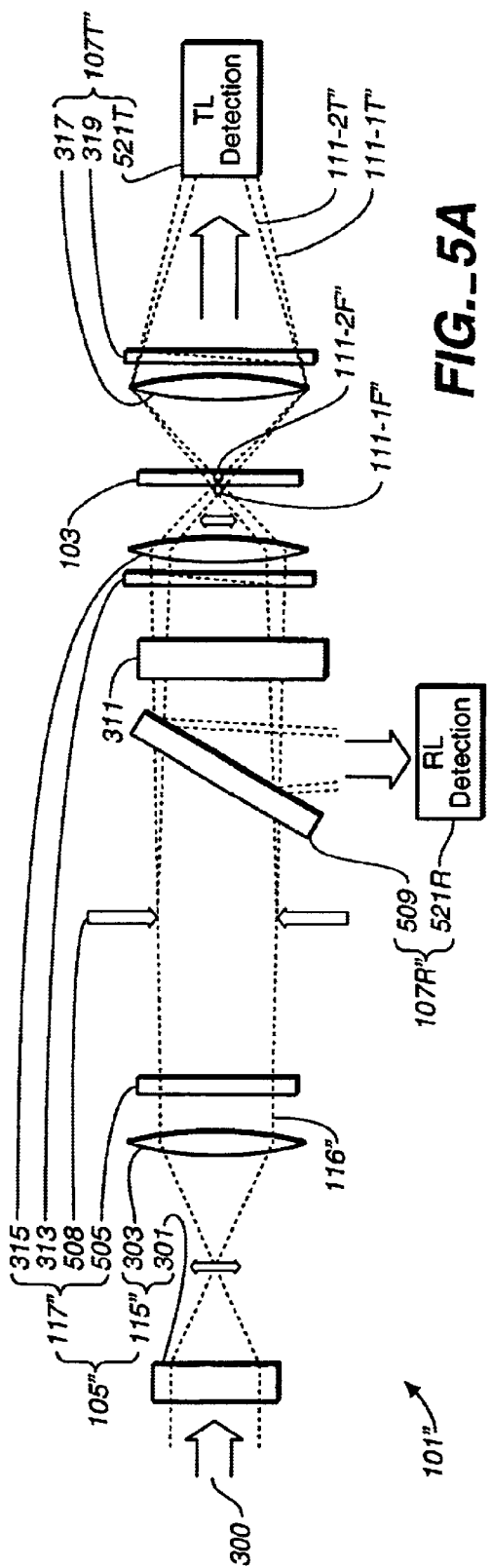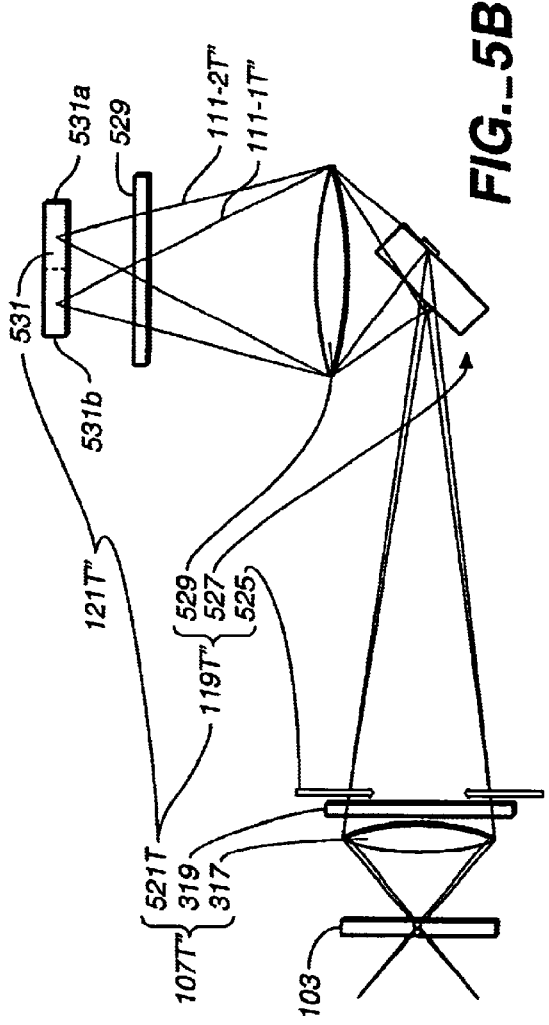

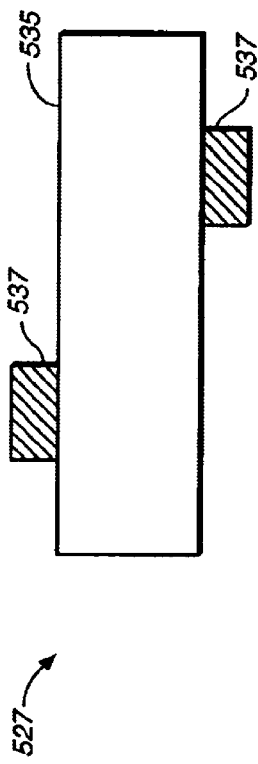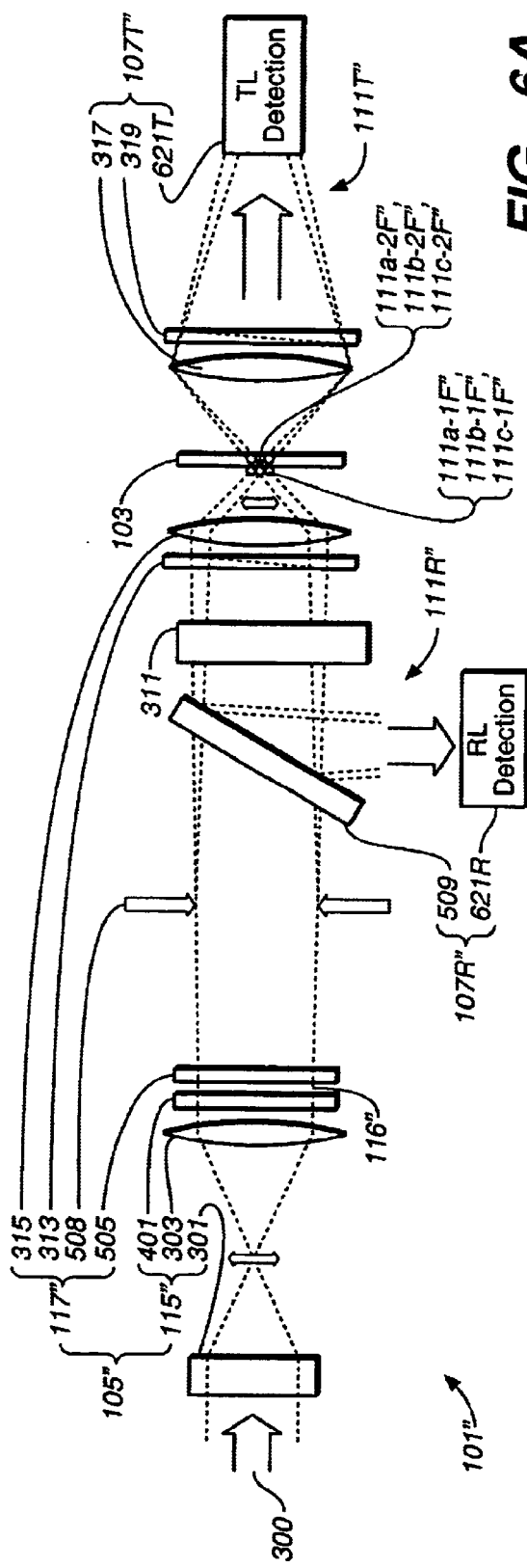

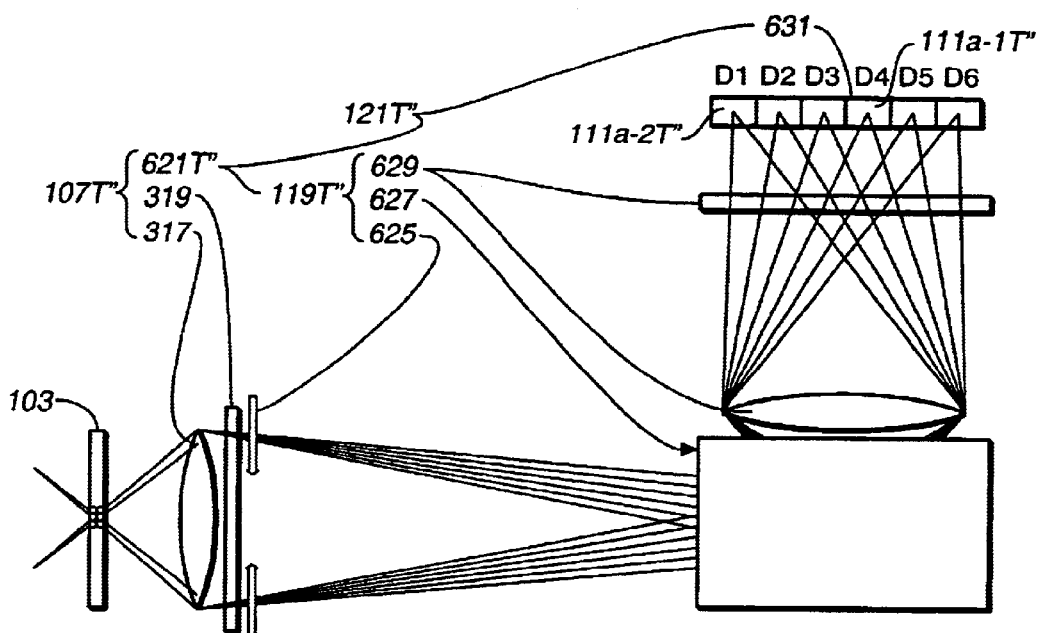
FIG._6B
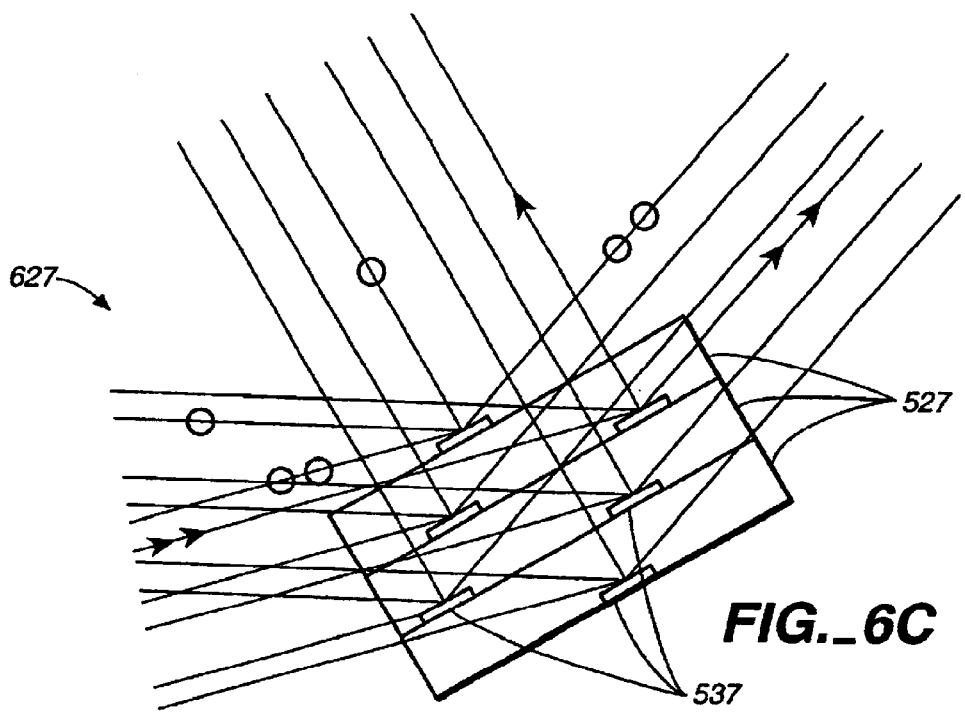
FIG._6C

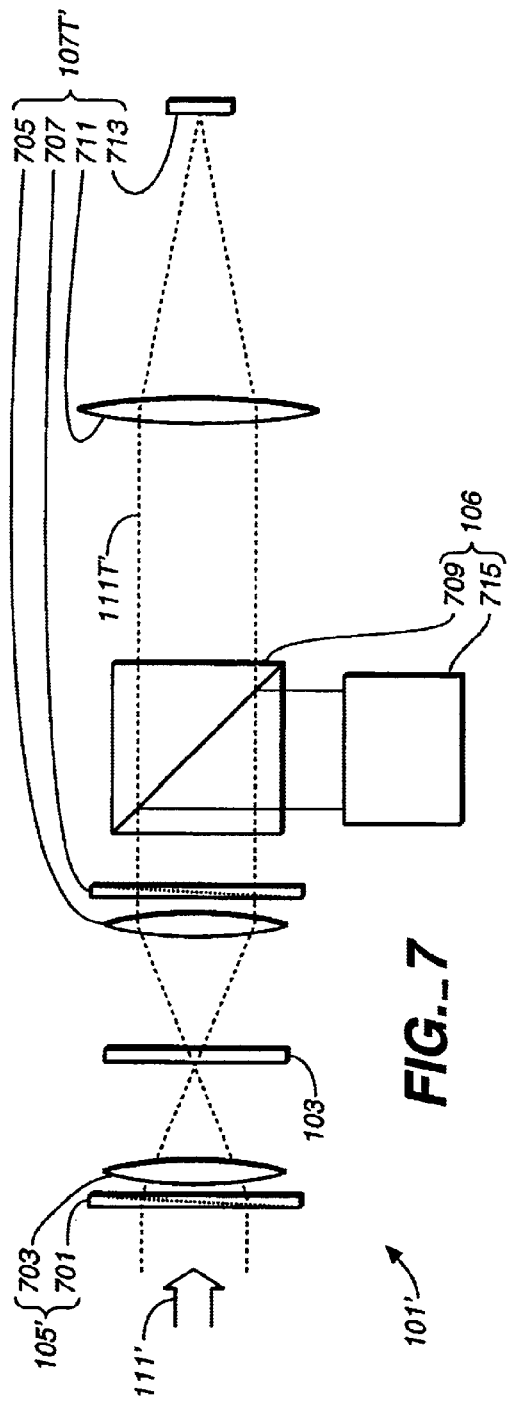
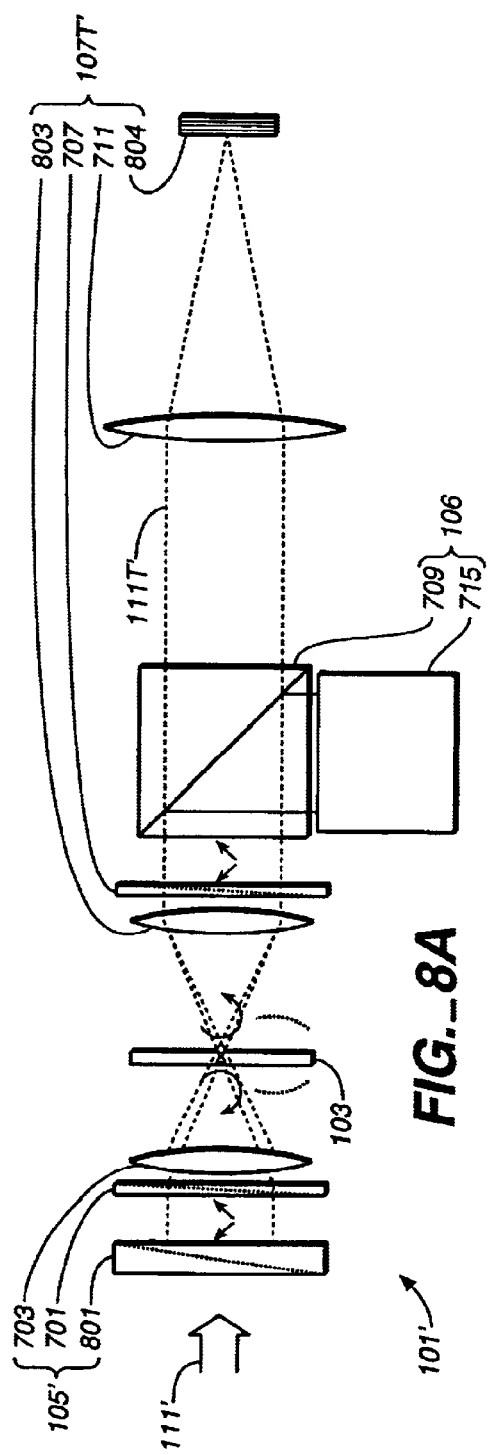
FIG._7
FIG._8A

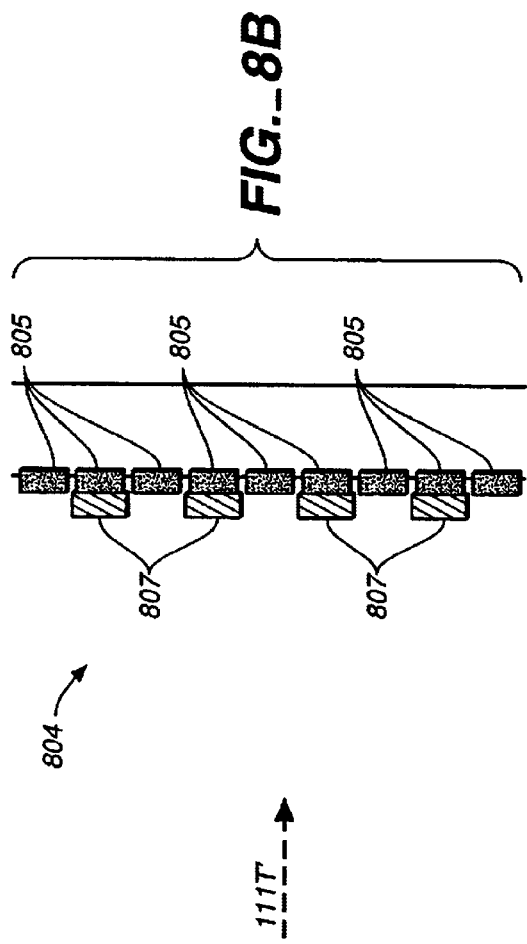
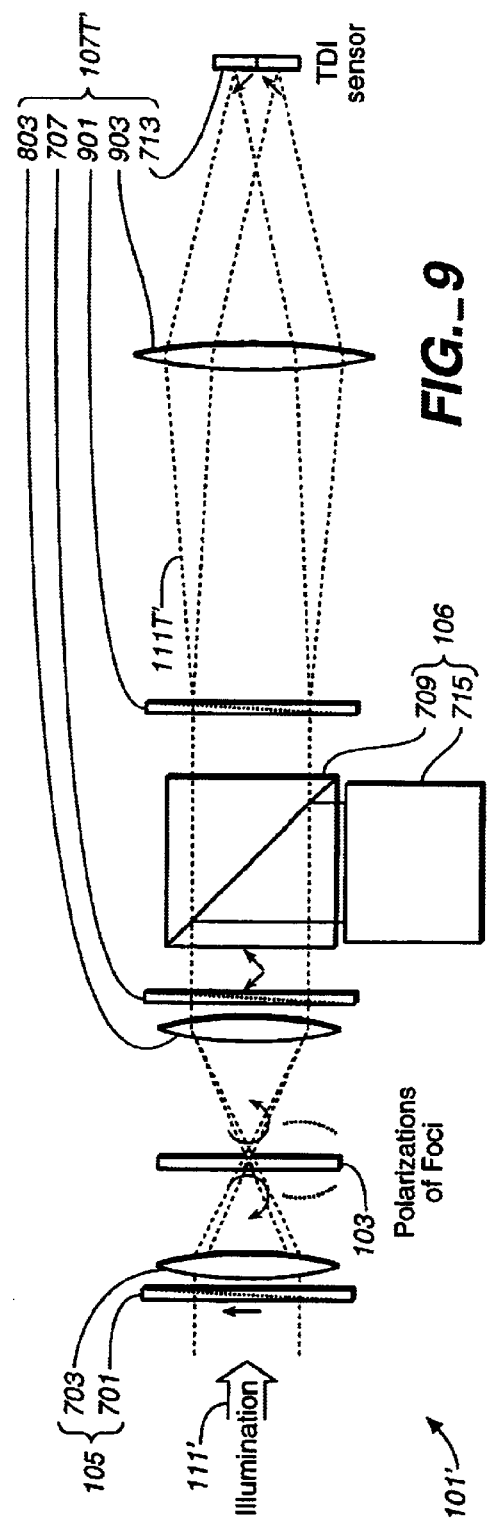

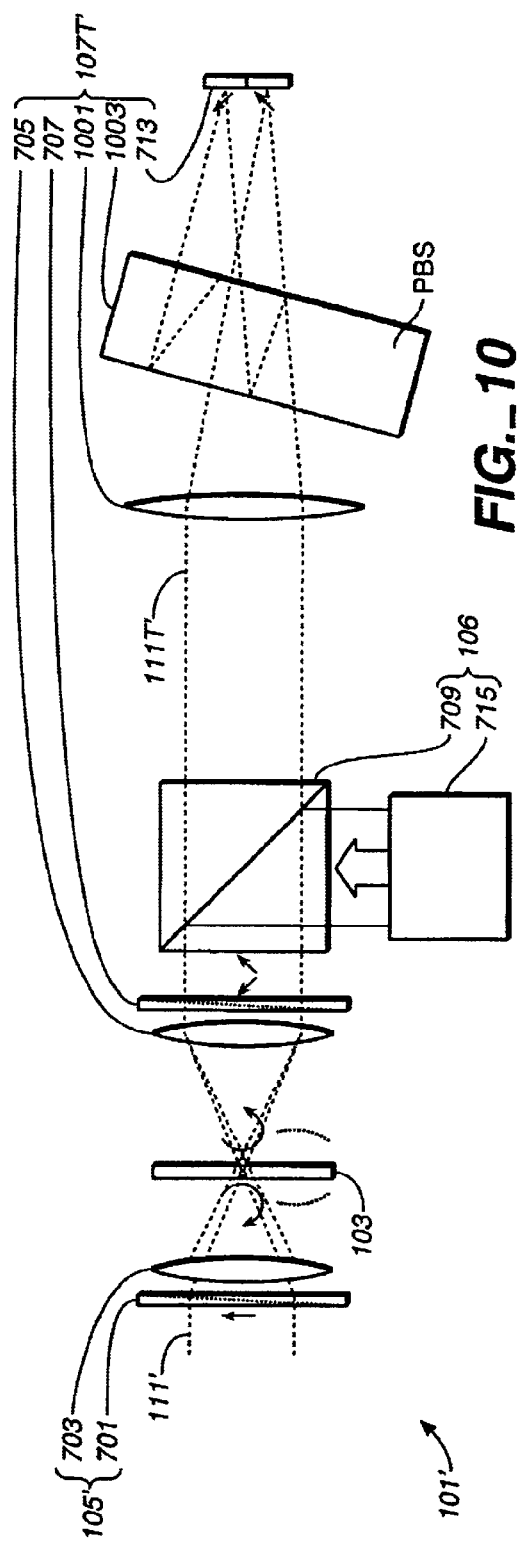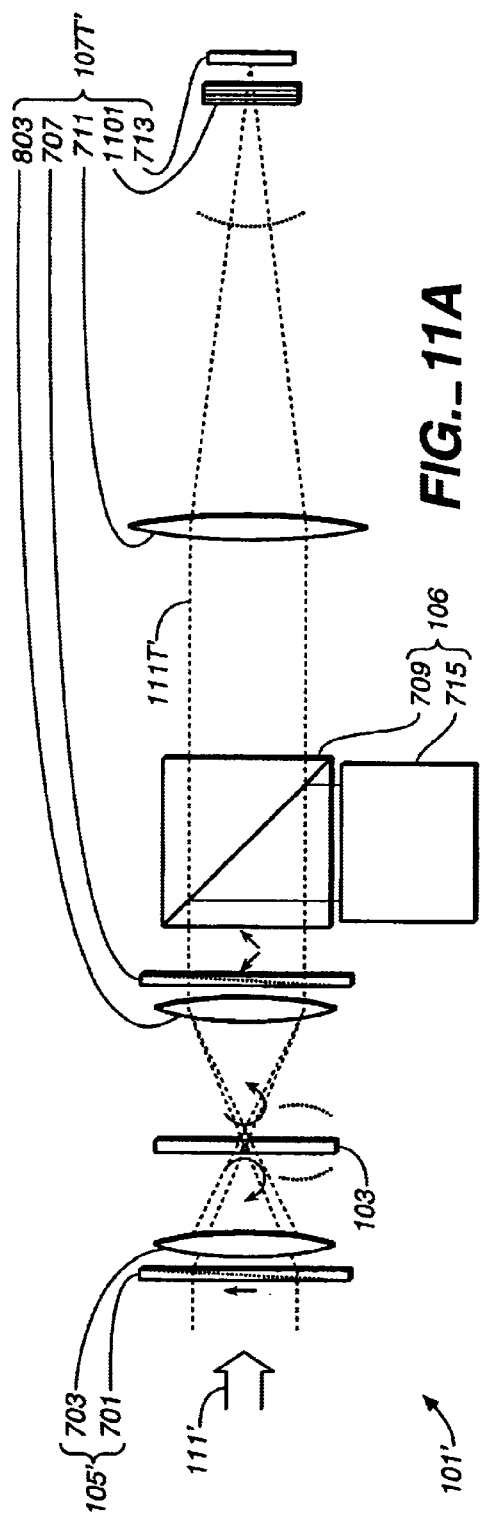

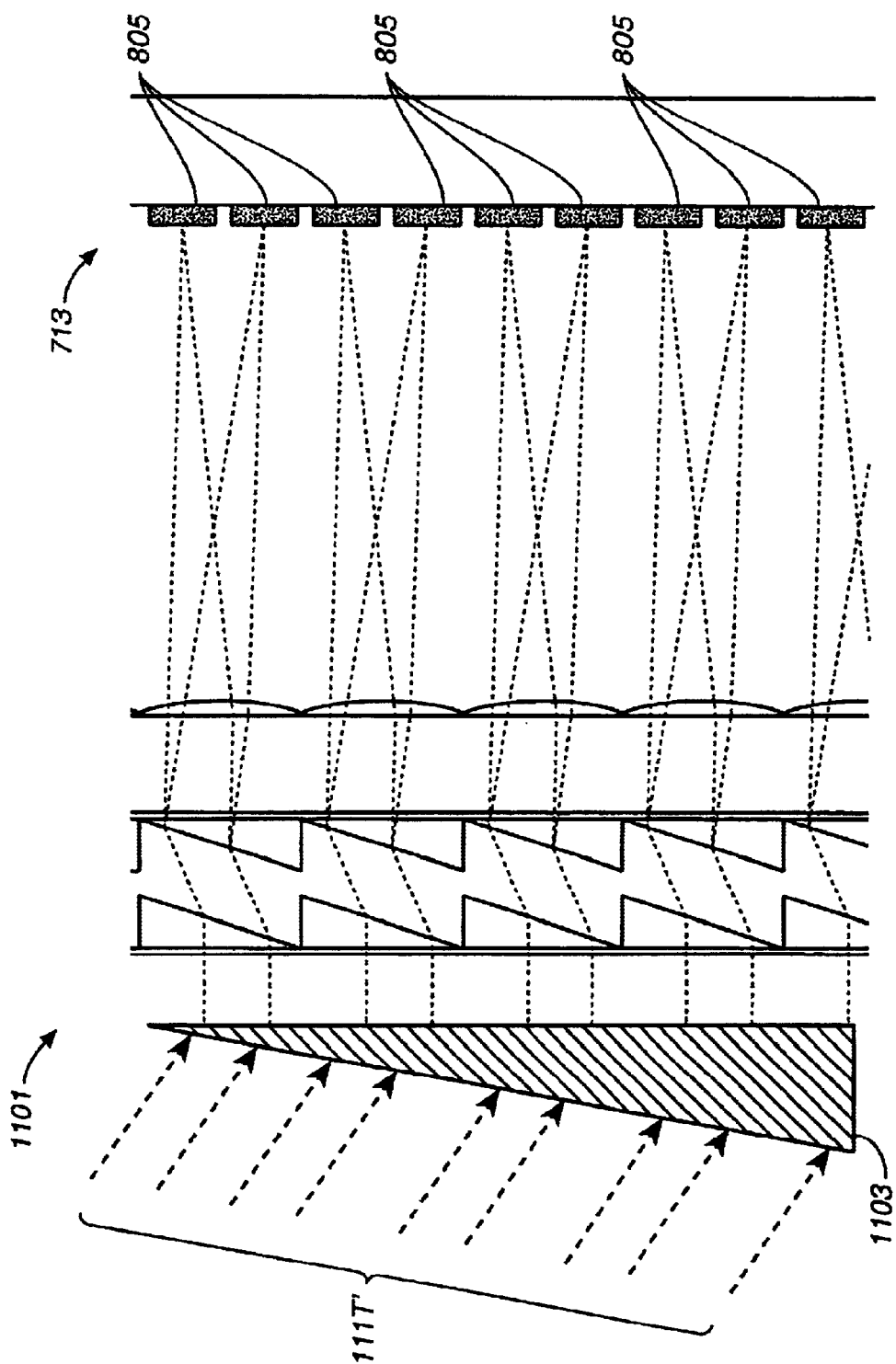
FIG._11B

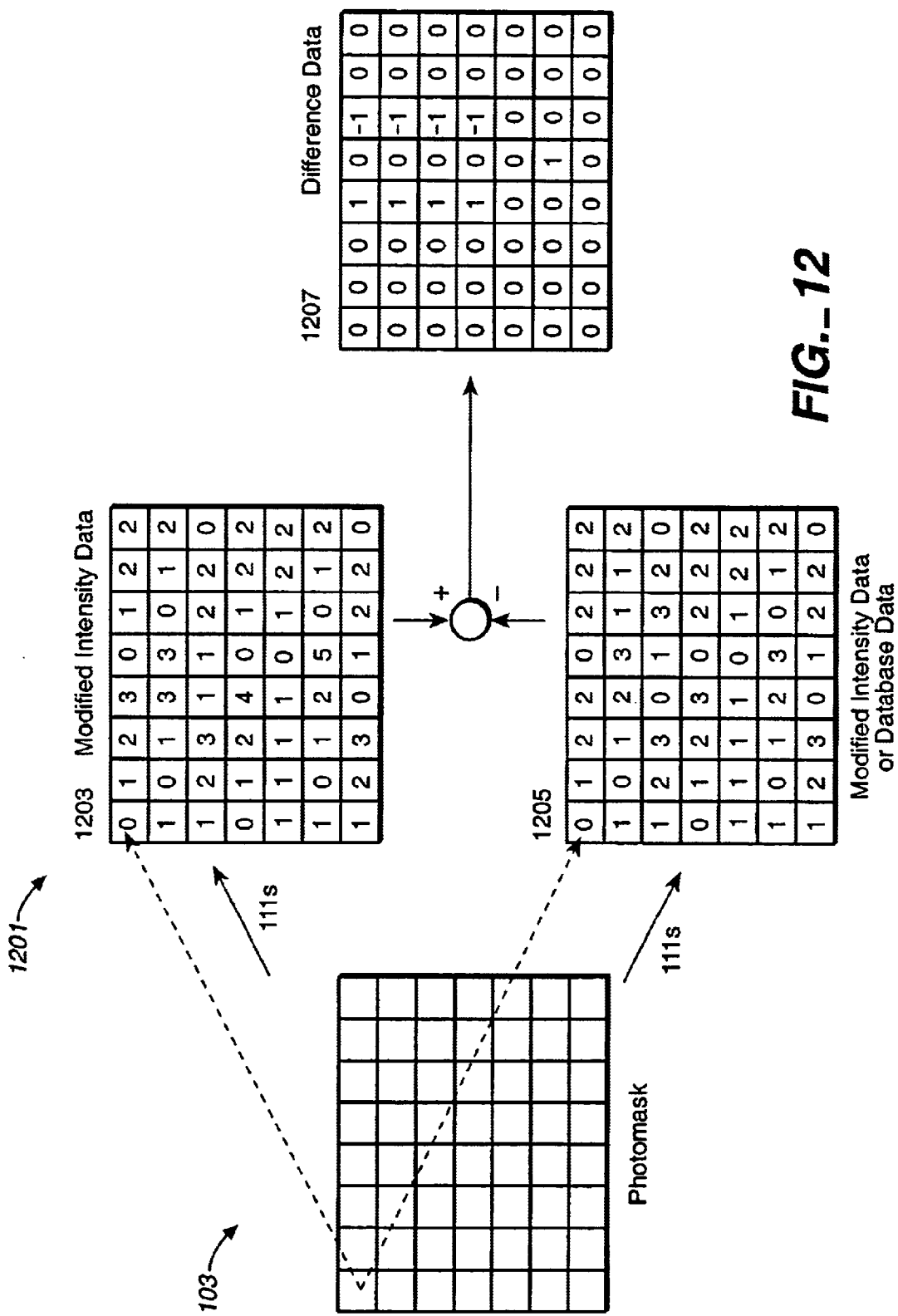
FIG._12

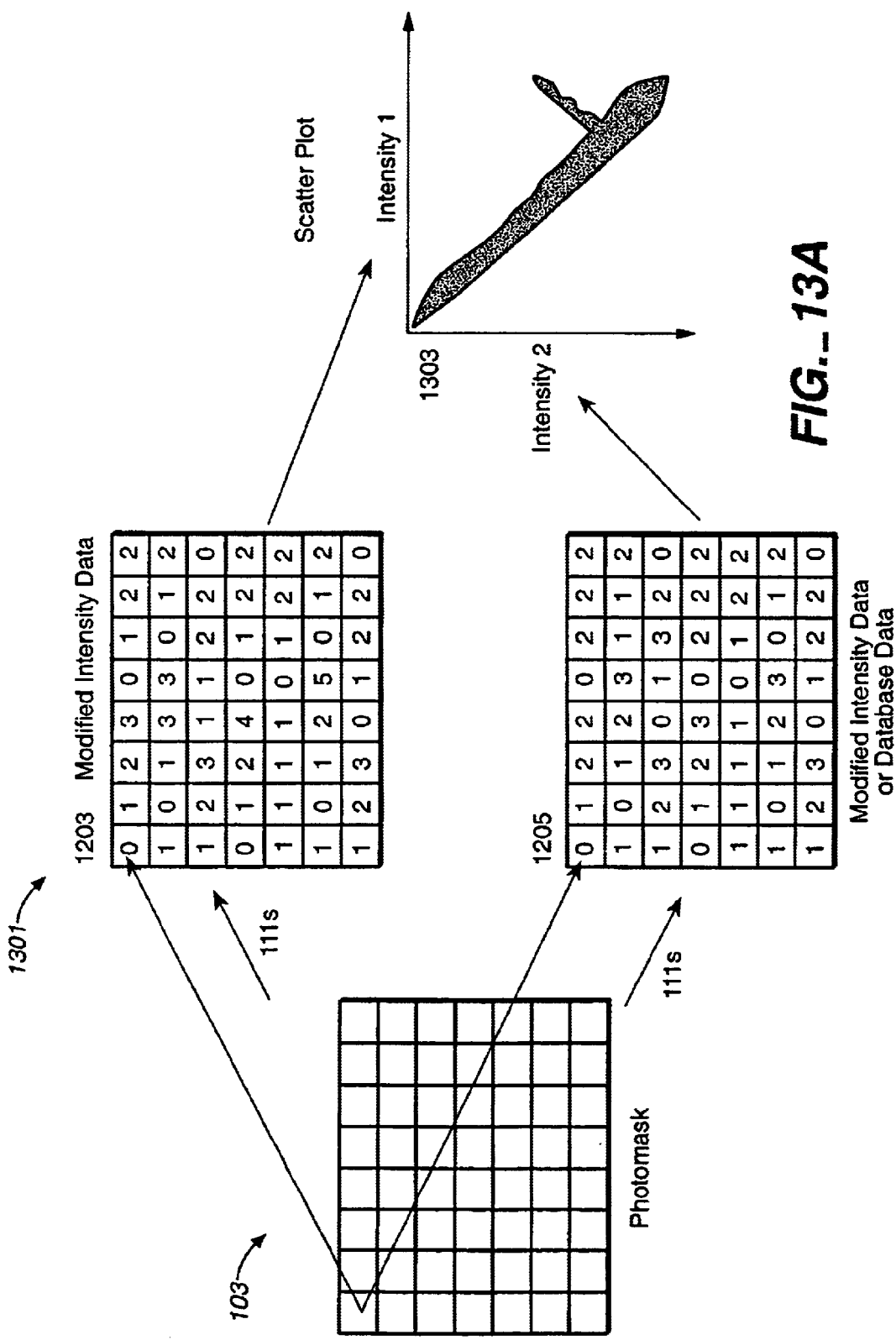
FIG._13A

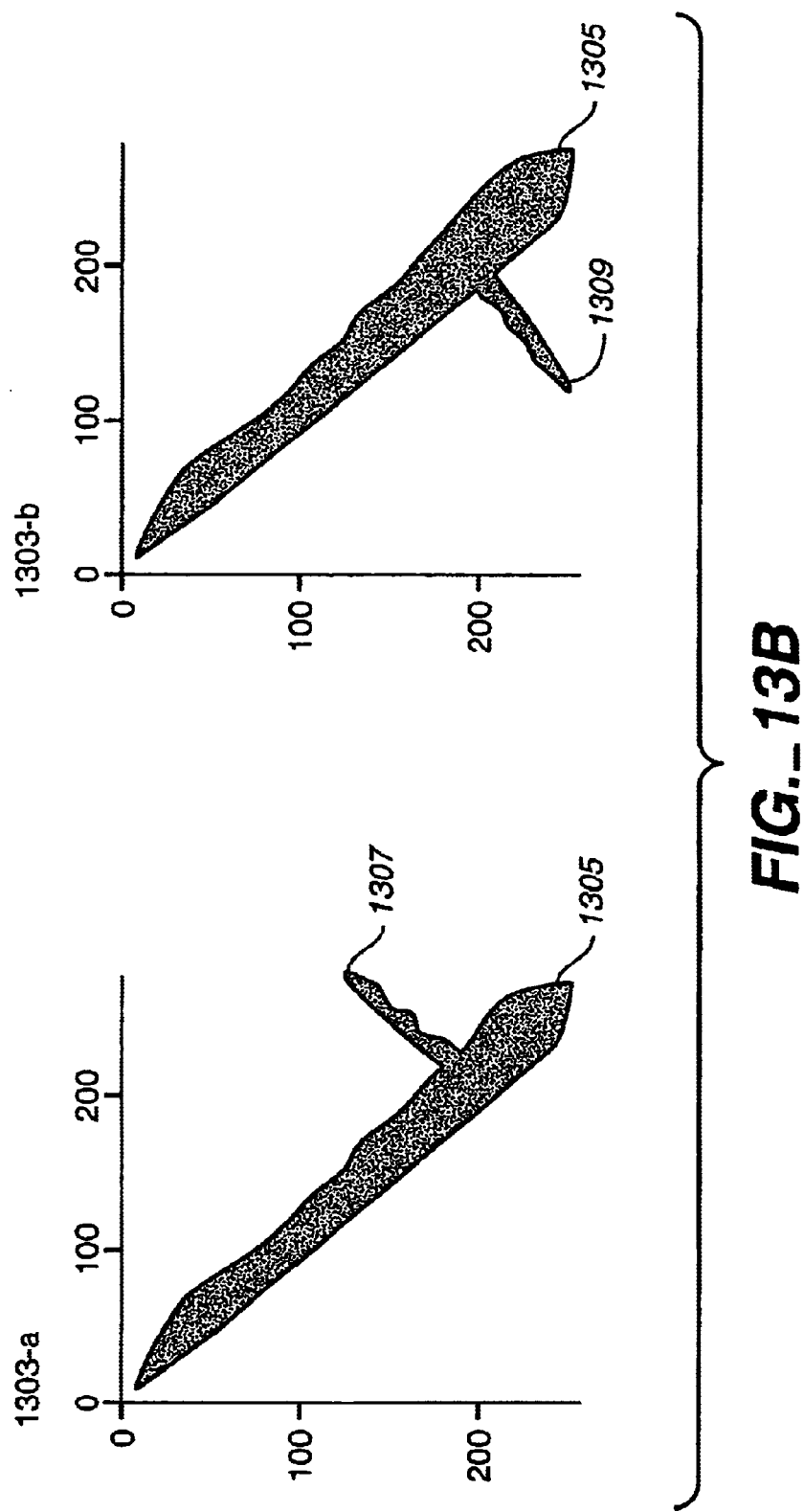
FIG._13B

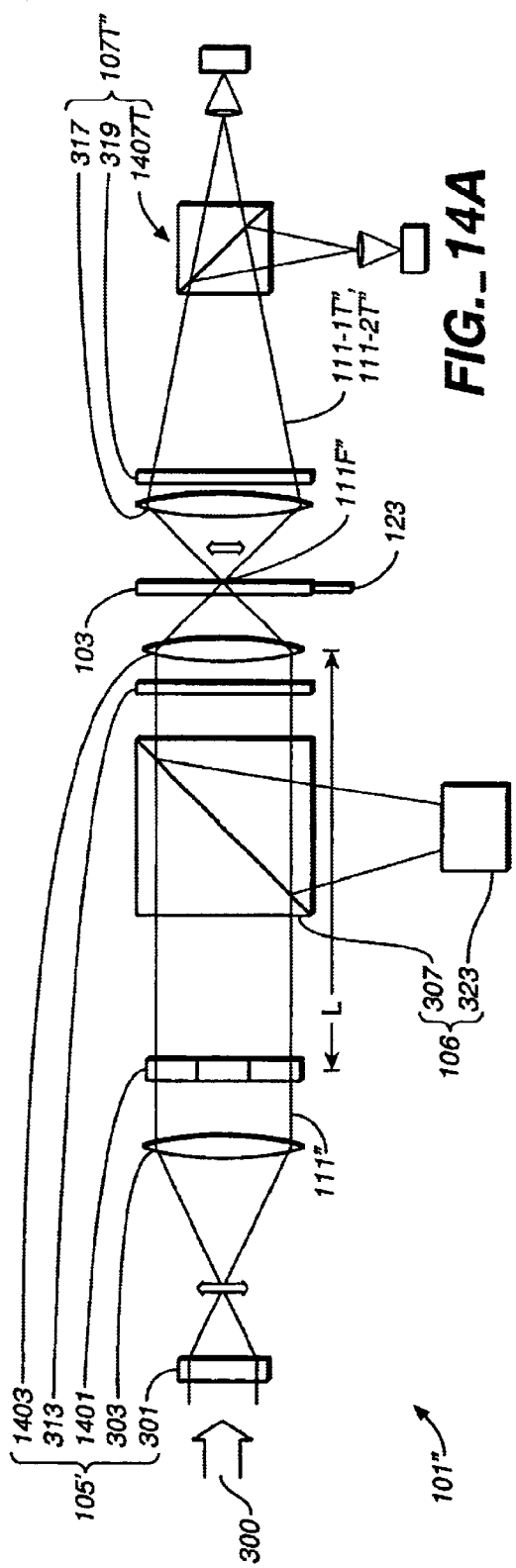
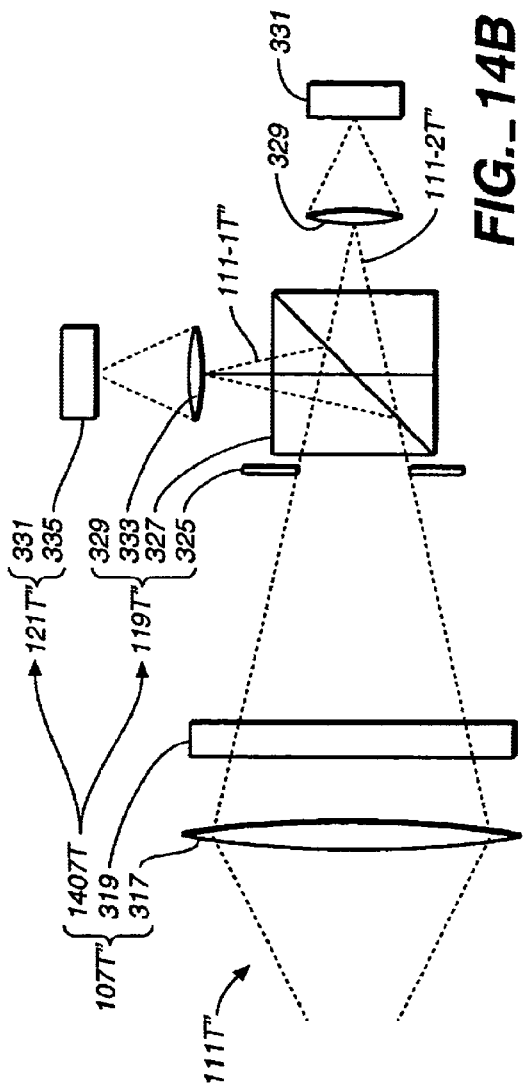
FIG._14A
FIG._14B

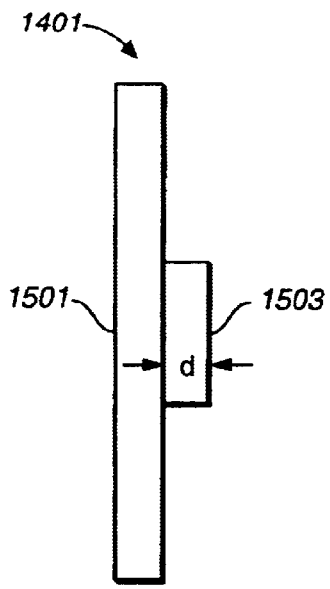
FIG._15A
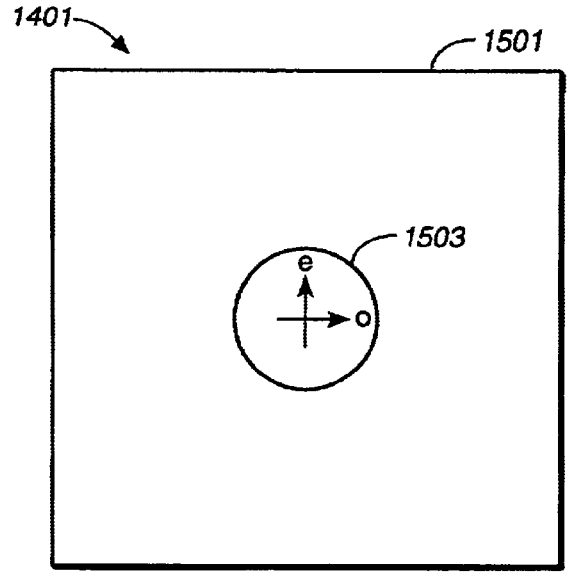
FIG._15B
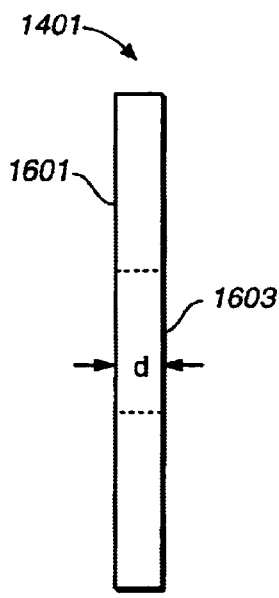
FIG._16A
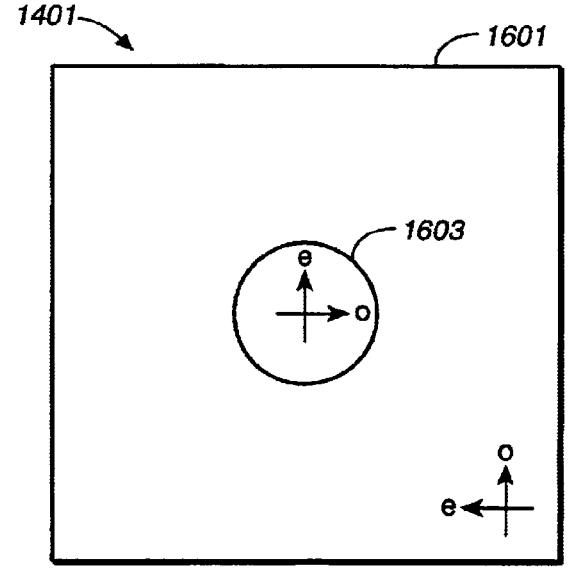
FIG._16B

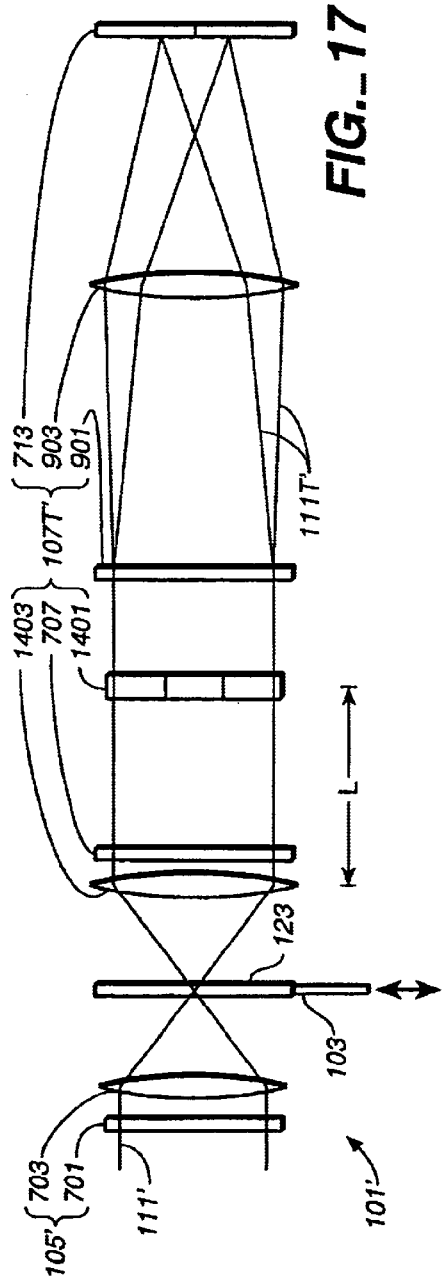
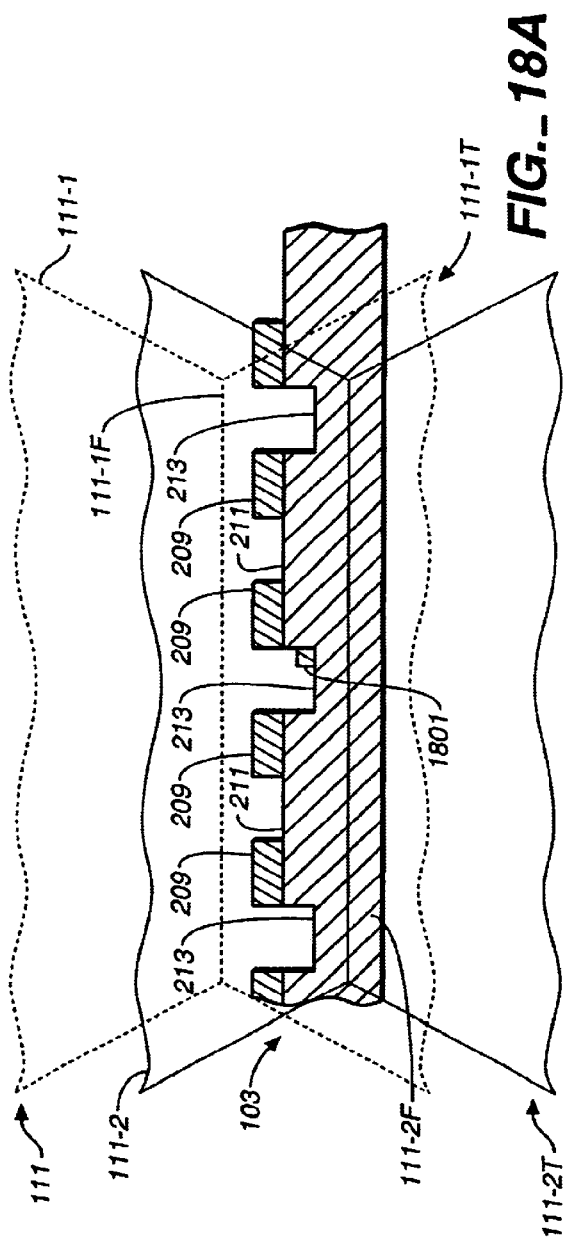

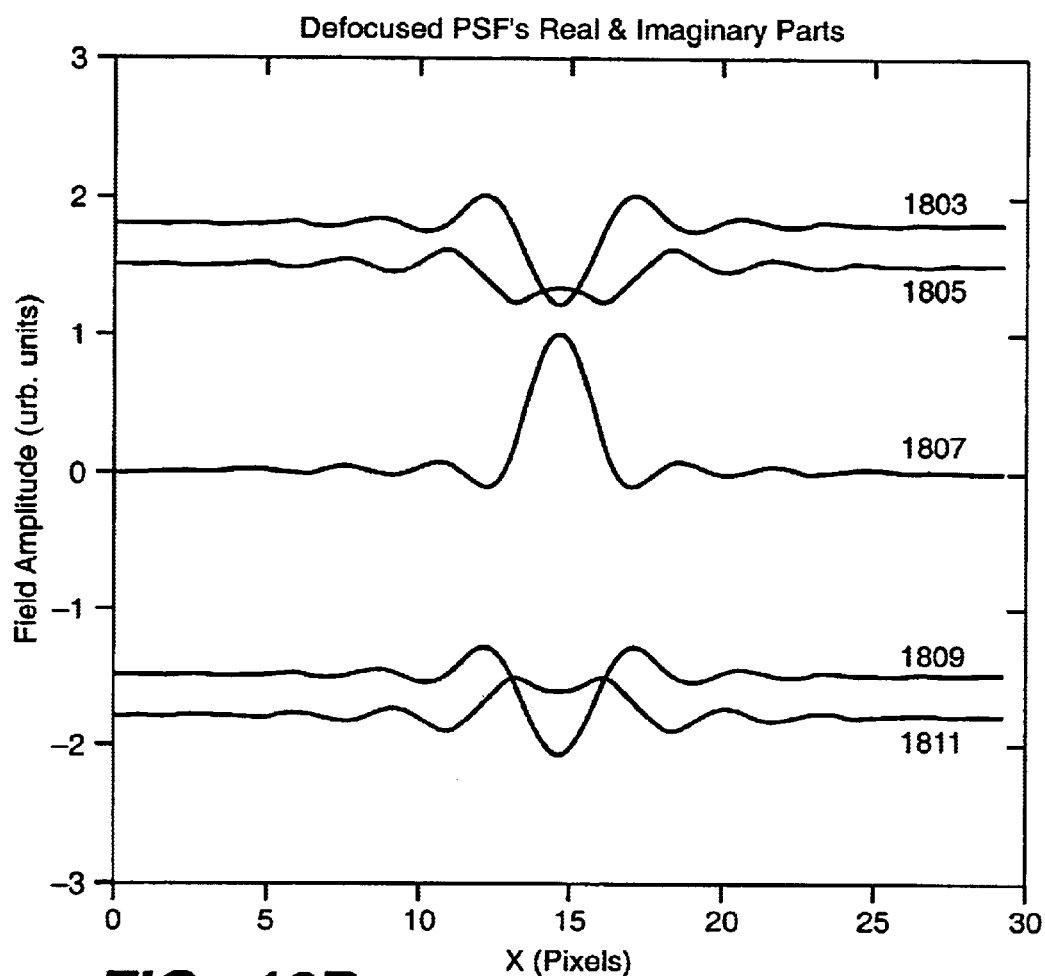
FIG._18B
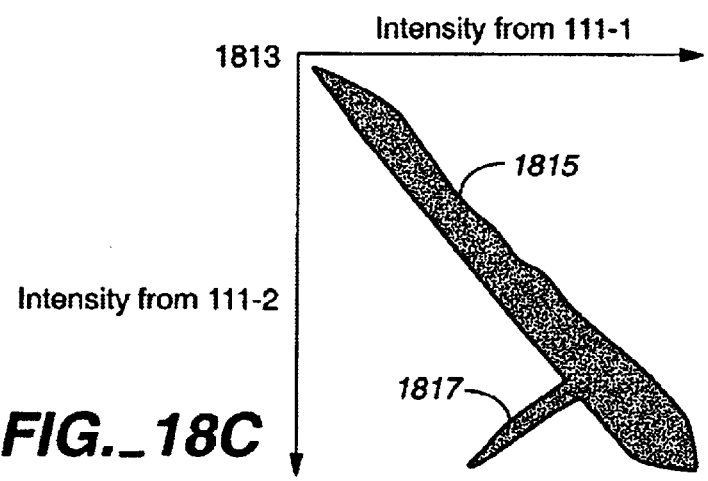
FIG._18C

EFFICIENT PHASE DEFECT DETECTION SYSTEM AND METHOD

FIELD OF THE INVENTION

The present invention relates generally to optical inspection systems, and more particularly to an automated photomask inspection apparatus for detecting or classifying defects that might occur on optical masks, reticles, and the like.

BACKGROUND OF THE INVENTION

Integrated circuits are comprised of three-dimensional structures of conductors, semiconductors and insulators formed on a semiconductor substrate or wafer. The integrated circuit manufacturing process typically involves multiple processing steps, including repeated transferring of patterns to the wafer surface using photolithography. Precise and defect free execution of each step is essential for the production of functional semiconductor devices at a yield that is economical for the manufacturer.

Photolithography is used to transfer a pattern to a wafer by exposing a photoresist-covered wafer to a light intensity pattern and developing the photoresist. The light intensity pattern is produced from the modification of an incident light beam having an optical wave front, with a photomask or reticle. The photomask includes features having variations in optical properties that modify the amplitude and/or phase of the incident beam through reflection, transmission, absorption or any combination thereof. The light is then projected onto the wafer to produce a required intensity pattern. One type of photomask feature is an amplitude object that modifies the amplitude, or intensity, of an illumination beam. For a transmission photomask, an opaque layer of metal film is one example of an amplitude object.

A second type of feature is a phase object that modifies the phase of an illumination beam or phase distribution of the optical wave front thus producing desirable intensity distributions in the image projected on the wafer. A transparent layer of varying thickness on a transmission photomask is one example of a phase shift object (or "phase shifter"). A phase-shift mask (PSM) has a pattern of phase shifters on the mask that results in an illumination beam comprised of phase variations. In practice, a PSM may contain either phase objects or a combination of amplitude and phase objects, as well as attenuated phase objects that simultaneously induce a phase and amplitude variation at select wavelengths. For a transmitted-light PSM, phase objects can be variations in the thickness of the photomask, usually a fused quartz plate. As the light travels from the photomask to the wafer, interference occurs between the differently phase-shifted portions of the illumination beam. The system optics, including the illumination source and photomask, produce an interference pattern of light and dark areas on the wafer.

Semiconductor industry roadmaps call for decreasing the critical dimension (CD) in semiconductor wafers. Phase shift mask technology can enable smaller CD's and is increasingly being used along with other approaches such as reducing the wavelength of the illumination beam or increasing the numerical aperture of the objective lens of the wafer stepper. Since most defects on a PSM will print, i.e. replicate itself, on every wafer in the particular semiconductor device, inspection for phase defects on PSMs is critical for achieving high yields. The industry is currently developing technologies to take advantage of the lower CDs of PSMs. These technologies include the ability to produce photomasks and the ancillary equipment and techniques for using and testing photomasks. In particular, most commercially available photomask inspection apparatus were designed before the widespread use of PSMs, as described for example, in U.S. Pat. Nos. 5,572,598 and 6,052,478, both to Wihl et al.

Of particular interest here is the inspection of masks that contain phase objects. Inspection of phase masks should include the detection and classification of the phase error, amplitude error of the phase shifter, amplitude error of adjoining features, and context. Since photomask inspection equipment usually performs an optical inspection at wavelengths and optical configurations different from that of the intended stepper, these differences must be taken into account.

The optical inspection of phase objects is technologically challenging. Pure phase objects modify the electromagnetic field of the incident light through changes in phase, and not of the intensity. As most detectors respond to variations in intensity, phase objects can be difficult to measure directly. Even more challenging is the detection of phase objects in the presence of amplitude objects. Due to the large amount of information contained on a mask, i.e. greater than $10^{15}$ pixels to write and greater than $10^{12}$ pixels to inspect a 6 inch mask, automated mask inspection systems are used.

A defect is defined here as any unintended modification to the intended photolithographic pattern caused during the manufacture of the photomask, or as a result of the use of the photomask. Defects can be due to, but not limited to, a portion of the opaque layer being absent from an area of the photolithographic pattern where it is intended to be present, a portion of the opaque layer being present in an area of the photolithographic pattern where it is not intended to be, chemical stains or residues from the photomask manufacturing processes which cause an unintended localized modification of the light transmission property of the photomask, particulate contaminates such as dust, resist flakes, cleaning residue, erosion of the photolithographic pattern due to electrostatic discharge, artifacts in the photomask substrate such as pits, scratches, and striations, and localized light transmission errors in the substrate or opaque layer.

Phase-shift photomask inspection systems should meet several requirements to be commercially successful. These requirements include the ability to: determine and report defects among about $10^{12}$ pixels in a reasonable time; inspect a single large die using gray-scale algorithms by rendering, from a database image of the PSM, both the transmission and phase for each pixel; handle multiple resolutions, including having a sensitivity to large (missing shifters) and small (sub-resolution) phase defects; process possible context information; account for off-wavelength inspection of phase errors; and distinguish between amplitude and phase objects. In addition to semiconductor applications, phase imaging systems are important in other fields, such as in the biological and medical areas.

Several imaging and defect detection systems for PSMs have been described in the prior art that address some of the above listed requirements. The following discussion provides information about several of the known techniques for obtaining phase information about objects useful in mask inspection systems.

Differential interference contrast techniques determine phase objects by interfering orthogonally polarized, laterally offset spots. Phase defects produce changes in the polarization state of the modified light that is detected as an intensity difference in the image, e.g. in a Nomarski microscope. Interference techniques have very high accuracy and can measure absolute phase. In practice however, interference techniques typically have very high alignment, optical wave-front quality, and system vibration requirements that are prohibitive or extremely costly to implement. Other problems include throughput and the need for a reference beam that could, in the case of the Nomarski technique, be blocked by chrome on the mask.

Differential phase contrast techniques, detailed in D. K. Hamilton and C. J. R. Sheppard, *J. Microscopy* 133, 27 (1984), determine the phase gradients of an object by the resulting intensity differences in the pupil plane of the imaging system measurable using a split or quad detector in the case of a scanner. Sensitivity of this technique depends on orientation of the phase object relative to the split detector that could result in missed defects.

The Zernike phase contrast technique uses a 90 degree shifted annular-pupil-plane filter to shift the $1^{st}$ order against $0^{th}$ order angular frequencies, making weak phase variations visible as intensity variations. For the case of an object with strong phase features, as in a phase shift mask, different pupil-plane filters may produce better sensitivity. However, Zernike-like imaging systems produce fringes in phase edge images, and are difficult to handle for database rendering in Die-to-Database (D:DB) inspection.

The defocused imaging approach generates an image using defocused optics. See, for example, C. J. R. Sheppard and T. Wilson, Phil. Trans. Roy. Soc. Lond. 295, 513 (1980), denoted as S&W in the remainder of this specification. Defocusing results in an imaginary transfer function that transforms phase variations to variations in amplitude. Prior art defocused imaging techniques for inspection of phase shift masks are not capable of handling arbitrary (i.e. non-repetitive), phase patterns, require a reference measurement to determine phase errors, or are limited to objects that can be resolved by the imaging system.

In aerial imaging, imaging parameters of the stepper are matched in the defect detection system, resulting in information on phase shifters. This is a low-resolution technique in which individual phase shifters are not resolved, and requires very high signal-to-noise ratios that are difficult and costly to implement in a high-speed imaging system.

Mach-Zehnder interferometry is an interferometric phase detection approach comparing the phase delay in the mask to the phase of external reference beam. As with other interference techniques, Mach-Zehnder techniques have alignment, optical wave front quality, and system vibration requirements that are prohibitive or extremely costly to implement.

While some problems in the detection of phase defects on a photomask have been addressed by the systems and methods disclosed above, there is still a great need to provide an efficient, highly sensitive phase defect detection system for a photomask that can be implemented at a reasonable cost. In particular, there is a need for a photomask inspection system that can determine the presence of phase defects, especially in the presence of amplitude objects, and that can be used to classify defects.

SUMMARY OF THE INVENTION

The present invention provides a novel method and system for optically measuring phase information in phase and amplitude objects that has many benefits over prior art techniques, particularly for the efficient inspection of photomasks or other articles having phase objects. In particular, many prior art limitations of phase object detection are surmounted with systems herein that inspect articles using one or more differently interacting illumination beams. In the present invention, the reflected or transmitted, or in general interacted or modified, beam(s) produce two or more responses that are different when illuminating the same area of the photomask or other articles that modify phase of the beam(s) depending on the presence of phase objects. The two or more responses are analyzed to provide two or more signals containing different phase information. The two or more responses may be produced simultaneously or sequentially from the interaction of the beam(s) with the article.

The present invention also provides methods and systems to inspect articles having phase objects by analyzing two or more signals containing different phase information generated by the interaction of the beam(s) with the objects in a manner that extracts the phase information from the amplitude information. The resulting system is thus sensitive to phase objects in the presence of amplitude objects, without greatly increasing the complexity of the optical system. For example, phase shift photomasks commonly contain amplitude objects, so that the present invention greatly simplifies detection of phase objects and phase defects on photomasks. In addition, the optical configuration of the present invention is particularly forgiving of variations in alignment and optical wave-front quality in comparison with prior art interferometric techniques. Also, the present invention is distinguished from other techniques in that it is capable of handling arbitrary (i.e. non-repetitive) phase patterns found in semiconductor photomasks.

In one embodiment, articles having phase objects are inspected by generating two or more signals resulting from the interaction and modification of illumination beams with the phase objects. The two signals are generated using systems, including but not limited to those having focus-based and Zernike-based optics, that are different for phase objects and amplitude objects, allowing for detection of one in the presence of the other using signal processing techniques. Another embodiment provides for a method and apparatus for classifying phase object defects using differently interacting beams. Comparison of information obtained using the interacted or modified beams provides information on the phase objects that can be used for inspection purposes, including, but not limited to the presence and classification of defects in a photomask or other articles in terms of defect size, phase error and context.

According to one particular embodiment of the invention, phase objects are inspected by supplying two illumination beams to an article that interacts differently according to variations in optical properties on the article. The different interactions can result from illumination beams that are differently focused or that have different Zernike point spread functions. The methods and systems of the present invention can be implemented using scanner-type or projector-type optical architectures, providing a variety of options for sequential, simultaneous, or multiplexed acquisition of the two signals or images. In addition, temporal, radial, or polarization separation can be used for creating and distinguishing the various signal or image channels in the latter two acquisition modes. For example, the different interaction of the two or more beams can result from the two beams having foci offset from one another that are used to inspect various locations on a photomask or other article. In illuminating the phase objects, these beams are differently focused (or defocused) from one another. Separation and measurement of the modified light provides sensitive information on the phase of objects at, and possibly near, the measurement location.

In one implementation of the above embodiment, a single focused illumination beam is used whose position is varied, relative to the photomask or other article, between two differently focused positions to obtain two signals of modified illumination beam intensity. Multiple scanning beams may be produced from a single beam from a radiation source. A birefringent lens and objective lens may be used to focus each of the scanning beams into pairs of differently focused traveling beams, which are separated after modification by the photomask. The individual modified beams may be separated according to characteristics of the individual beams, such as by their polarizations. An alternative implementation uses a multifocal zone plate at the system pupil and an objective lens to produce pairs of differently focused beams for each input beam, followed by spatial filtering to separate the individual modified illumination beams.

According to yet another particular implementation of the above embodiment, one or more illumination beams are converted to pairs of illumination beams slightly defocused relative to each other. The resulting pair of illumination beams is focused onto the same approximate area of the article. Illumination beams modified by the article are separated, producing signals representative of each modified illumination beam, and the individual pairs of signals are compared to provide phase information. The pairs of illumination beams may be scanned across the photomask to produce a map of the phase difference induced by the illumination beams. The comparison of pairs of differently focused signals provides information is less sensitive to amplitude objects than that provided by other phase detection techniques, and is capable of detecting phase differences of 30 degrees or less. In addition, three other implementations alternatively call for 1) using a single illumination beam, 2) one pair of illumination beams, or 3) multiple pairs of illumination beams. Thus the novel features of the present invention may be implemented using a variety of optical systems for focusing a beam at approximately the same position on a photomask or other article, but at different depths through the article.

In another particular embodiment of the present invention, photomasks are inspected using two or more beams results from beams having different Zernike point spread functions. Thus, for example, coaxial beams having complementary plus and minus 90 degree point spread functions are modified by an article according to phase objects thereon. The different point spread functions may be introduced, for example, by a Zernike plate at the back focal plane of an objective, where such introduction can occur prior to or after interaction of the beams with the photomask. The two images of the article produced thereby can be separated and compared according to their corresponding locations. Inspection using complementary point spread functions (such as by using Zernike plates) provides increased sensitivity to phase objects over prior art Zernike methods.

It is another aspect of the present invention to provide a method and apparatus for detecting phase object defects in photomasks by comparing one defocused image with a database of expected defocused image data. Comparison of the interacted beam with the database provides information on the phase objects that can be used for inspection purposes, including, but not limited to the presence and classification of defects in a photomask.

A further understanding of the invention follows from the detailed discussion of specific embodiments below. This discussion refers to devices, methods, and concepts in terms of specific examples. However, the method of the present invention may operate with a wide variety of devices. It is therefore intended that the invention not be limited by the discussion of specific embodiments.

All publications and patents cited herein are hereby incorporated by reference in their entirety for all purposes. Additional objects, advantages, aspects and features of the present invention will become apparent from the description of preferred embodiments, set forth below, which should be taken in conjunction with the accompanying drawings, a brief description of which follows.

BRIEF DESCRIPTION OF THE DRAWINGS

FIG. 1A is a schematic of some of the main components of a photomask inspection system according to the present invention.

FIG. 1B provides details of an example of a scanning-type photomask inspection system according to the present invention.

FIG. 1C is a schematic of a an example of a projection-type photomask inspection system according to the present invention.

FIG. 2 is a sectional view of the inspection apparatus of the present invention as applied to the inspection of a Levenson-type PSM.

FIG. 3A is a ray diagram of a first embodiment of a scanning-type, focus-based photomask inspection apparatus of the present invention.

FIG. 3B is a ray diagram of the first embodiment collection system for transmitted light.

FIG. 4A is a ray diagram of the second embodiment of a scanning-type, focus-based photomask inspection apparatus of the present invention.

FIG. 4B is a ray diagram of the second embodiment collection system for transmitted light.

FIG. 5A is a ray diagram of the third embodiment of a scanning-type, focus-based photomask inspection apparatus of the present invention.

FIG. 5B is a ray diagram of the third embodiment collection system for transmitted light.

FIG. 5C is a ray diagram of the spatial filter of the third embodiment.

FIG. 6A is a ray diagram of the fourth embodiment of a scanning-type, focus-based photomask inspection apparatus of the present invention.

FIG. 6B is a ray diagram of the fourth embodiment collection system for transmitted light.

FIG. 6C is a ray diagram of the spatial filter of the fourth embodiment.

FIG. 7 is a ray diagram of a fifth embodiment of a projection-type, focus-based inspection apparatus of the present invention.

FIG. 8A is a ray diagram of the sixth embodiment of a projection-type, focus-based inspection apparatus of the present invention.

FIG. 8B is a schematic of a TDI detector modified to accept two images.

FIG. 9 is a ray diagram of the seventh embodiment of a projection-type, focus-based inspection apparatus of the present invention.

FIG. 10 is a ray diagram of the eighth embodiment of a projection-type, focus-based inspection apparatus of the present invention.

FIG. 11A is a ray diagram of the ninth embodiment of a projection-type, focus-based inspection apparatus of the present invention.

FIG. 11B is a schematic of a TDI detector and array for delivering two overlapping images onto the array according to the fifth embodiment of a projector-type apparatus.

FIG. 12 is a flow diagram for obtaining phase information using differencing.

FIG. 13A is a flow diagram for obtaining phase information using scatter plots.

FIG. 13B shows representative scatter plots of the present invention.

FIG. 14A is a schematic of a tenth embodiment of a scanning-type, Zernike-based inspection apparatus of the present invention.

FIG. 14B provides details of the reflected-light detection system of the first embodiment of a scanning-type, Zernike-based inspection apparatus.

FIG. 15A is a side view of a first embodiment Zernike plate of the present invention.

FIG. 15B is a front view of a first embodiment Zernike plate of the present invention.

FIG. 16A is a side view of a second embodiment Zernike plate of the present invention.

FIG. 16B is a front view of a second embodiment Zernike plate of the present invention.

FIG. 17 is a schematic of an eleventh embodiment of a scanning-type, Zernike-based inspection apparatus of the present invention.

FIG. 18 is an embodiment of the data analysis system of the present invention for a focus-based optical system, where FIG. 18A is a sectional view of a Levenson-type PSM with a phase defect, FIG. 18B is a plot of the modified light intensity from the two, differently focused illumination beams, and FIG. 18C is a scatter plot of the modified light intensities.

Reference symbols are used in the figures to indicate certain components, aspects, or features shown therein, with reference symbols common to more than one figure indicating like components, aspects or features shown therein. The reference symbols used herein are not to be confused with any reference symbols used in the items that have been incorporated herein by reference.

DETAILED DESCRIPTION OF THE INVENTION

The present invention is related to methods and systems for inspecting a phase-shift-producing article from beam(s) that interact differently with the article. By way of convenience, the invention is described in terms of a method and system for determining defects in a semiconductor photomask. It will be understood by those skilled in the art that the invention is applicable to measurements on other types of photomasks and on other phase-inducing articles, such as biological materials. In addition, the embodiments described herein include functions performed by various components or combinations of components. Specifically, the methods and systems of the invention provides for various optical, control, and data analysis functions. It will become obvious to those skilled in the art that the present invention can be practiced with other or equivalent components, and that as such the claimed invention is intended to incorporate these equivalent structures. As such, the scope and bounds of the invention should not be limited except as provided in the attached claims.

The following discussion provides an overview of the invention, followed by a discussion of optical inspection of photomasks, some optical design considerations, followed by some specific embodiments and lastly analysis of data according to the present invention.

Areas on an article such as a photomask are illuminated with one or more illumination beams that interact with the same photomask position, collecting each of the beams after modification by the photomask, obtaining at least two signals containing different phase information due to the modification and representative of the intensity of the modified beams, and analyzing the signals according to the location at which the beam was modified. The analyzed signals can be related to features on the photomask at the location, forming the basis for the inspection.

There are several optical configurations that provide at least two signals for determining photomask phase information. Configurations can be constructed based on, but not limited to, differences in focal planes, point spread functions, including Zernike point spread functions, polarizations, and combinations thereof. The two signals may be produced by illuminating the photomask by two beams simultaneously, or by illuminating the photomask by a single beam sequentially. Where an embodiment is described hereinbelow by providing two or more beams to illuminate a photomask simultaneously in order to produce the two or more signals having different phase information, it will be understood that there is a corresponding alternative embodiment similar to such embodiment in all respects except that it would employ a single beam to illuminate a photomask sequentially; all such variations are within the scope of the invention. The beam(s) employed contains radiation or light of wavelength(s) in the visible, infrared, and/or ultraviolet ranges.

By way of convenience, the invention is described in terms of focus-based and Zernike-based systems. In focus-based systems, two illumination beams are focused differently onto the photomask. As will be shown subsequently, the light interacts with the photomask according to the focus of individual illumination beams, and combining indications of the two modified beams provides greater sensitivity than prior art systems. In Zernike-based systems, an objective lens and a Zernike phase plate cooperate to either illuminate or to collect modified illumination beams and produce pairs of signals.

Inspection of photomasks with optical systems of the present invention produces two signals containing different phase information for each inspection point, where the difference in phase information of the two signals depends on different modification of the beam(s) by phase and amplitude objects on the photomasks. The differing response to the same phase and amplitude objects permits the application of signal processing techniques to determine phase objects in the presence of amplitude objects. Of particular interest are differing responses that, when combined, emphasizes phase objects and de-emphasizes amplitude objects.

Also, by way of convenience, the invention is described in terms of scanning-type and projector-type systems. In a scanner-type system, a coherent source produces a spot that is scanned across the photomask, a detector collects the transmitted or reflected light, and the resulting partially coherent image is assembled electronically. In this case, the scanner optics largely defines the image quality while the detection optics serves as a "light bucket" and for setting the partial coherence. In a projector-type system, an incoherent area illumination system illuminates a section of the photomask, which the imaging system images onto an image forming area detector.

The images of a scanner-type and projector-type system are nominally equivalent. In focus-based systems, for example, defocused scanner images are produced by defocusing the scanning illumination beam, whereby the focus of the light collection system is not critically important. Projector images are produced by defocusing the imaging optics between the photomask and the area detector, whereby the focus of the illumination system is not critical.

The scope of the present invention covers numerous optical configurations for illuminating the photomask and collecting the modified light, as well as methods for analyzing the intensity measurements. The following discussion presents a description of general embodiments of the present invention. Primed numbers indicate components that are specifically used or tailored for use in projector-type systems, while double primed numbers indicate those for scanning-type systems.

The general schematic of FIG. 1A illustrates several of the features of many of the embodiments of a photomask inspection system of the present invention. In particular, FIG. 1A can represent a focus-based or Zernike-based system, as well as scanning or projector architecture. As shown in FIG. 1A, an optical inspection system 101 is adapted to receive a photomask 103 for inspection. The optical inspection system 101 includes an illumination system 105 for generating at least one illumination beam 111, a transmitted-light collection system 107T, a reflected-light collection system 107R, a computer control system 109, and a data analysis system 125, which may simply be an image computer. The illumination beam 111 is incident on the photomask 103 and is modified by the photomask surface. Specifically, each illumination beam 111 is transmitted through the photomask 103 and becomes a modified, or transmitted, illumination beam 111T and is also reflected from the photomask, becoming a reflected illumination beam 111R. While both transmitted-light collection system 107T and reflected-light collection system 107R are shown in FIG. 1A and both may be used to produce the two or signals containing different phase information as described herein, it will be understood that the use of only one of the two systems may be adequate and is within the scope of the invention. Where only one of the two types of collection systems is described in an embodiment herein, it will be understood that the other type of collection system is possible and is within the scope of the invention.

The illumination system 105 and collection systems 107 work together to illuminate photomask 103, to produce differently modified illumination beams, and to separate the beams after modification. The cooperation between illumination system 105 and collection systems 107 includes, but is not limited to, methods and systems for: separating modified beams, for example, by polarization or spatially; collecting data, for example using scanning or projector architecture; and producing differently modified beams, for example using multiple differently focused beams or using Zernike optics to detect phase objects.

Examples of the present invention implemented as scanning-type and projector-type systems are shown in FIGS. 1B and 1C, respectively. For the scanning-type system 101" of FIG. 1B, the illumination system 105" produces a scanning beams 111", which is transmitted through the photomask 103 as transmitted beams 111T". The illumination system 105" includes an illumination source 115" and a difference inducing and focusing optics 117" that is comprised of a difference-inducing optics 117a" and an objective 117b". The difference-inducing optics 117a" induce differences in the illumination beams that form the basis for separation in the collection system 107T. Specific embodiments will include, but are not limited to, differences in focus (focus-based systems) and differences in Zernike point spread function (Zernike-based systems). A collection system 107" includes collection optics 117T" and a detection system 122T" comprising separation optics 119T" and one or more detectors 121T". Since the photomask 103 is scanned, it may be advantageous to have more than one scanning spot at a time (that is, have N>1) to reduce the total scanning time. For scanning-type systems, N pairs of beams are used to provide N multiple beams 116" to produce N scanning spot with the objective 117b".

In many applications, it is preferable to perpendicularly illuminate the photomask 103, and thus the pair of reflected beams 111R" and the pair of illumination beams 111" are coaxial. The N pairs of reflected beams 111R" are focused by the focusing optics 117b", and are diverted by beam splitter 127" through separation optics 119R" and onto detector 121R". Alternatively, a beam splitter could be placed between the photomask 103 and objective 117b", appropriately changing the reflected light collection optics. Normal illumination of the photomask 103 is preferred because the illumination beam(s) would then be rotationally symmetric with respect to the photomask, and one does not have to take into account the orientation of any pattern or lines on or in the photomask relative to the direction of the illumination beam(s). Normal illumination also provides improved imaging characteristics. Where reflected radiation is collected using system 107R", normal illumination is preferable since the same objective 117b" in the illumination optics may be used in such collection system. It will be understood, however, that oblique illumination is possible and is within the scope of the invention.

In the scanning-type system 101" of FIG. 1B, the illumination system 105" produces a scanning beam(s) 111", which is transmitted through the photomask 103 as transmitted beam(s) 111T". The collection system 107T" includes collection optics 108T" and a detection system 122T" comprising separation optics 119T" and one or more detectors 121T". The N pairs of transmitted beams 111T" are collected by collection optics 117T", separated into separate modified illumination beams by the separation optics 119T", and delivered to the one or more detectors 121T". The detectors 121T" return the pair of signals 111s", where each signal is proportional to the intensity of each one of transmitted beams 111T".

For the projector-type system 101' of FIG. 1C, the photomask is imaged with either one illumination beam or one illuminating beam pair (N=1) 111' from illumination system 105'. Transmitted beam 111T' is focused with objective 129' onto a one or two-dimensional separation and imaging detector 131', which generates signals 111s' corresponding to the modification of light over an area of the photomask 103. For projector-type systems of the present invention, multiple images are obtained at the same approximate photomask area. While the scanning-type system collects modified beams over one or more spot-sized illumination areas, the projector-type system flood illuminates a larger area of the photomask and images the illuminated area and thus can be used to collect information over a greater photomask area.

While the schematic of FIG. 1A illustrates inspecting a photomask using both transmitted and reflected light, the multiple illumination optical configuration of the present invention provides useful and informative data in either the reflected or transmitted mode, and thus it is to be understood that the present invention can be used to inspect objects using reflected light, transmitted light, or a combination thereof. Inspection of the photomask thus results from analysis of either one or both of beams 111R and 111T. According to the specific method of inspection, one or both of light collection systems 107T and 107R each produce signals 111s that are representative of the intensity of the respective modified illumination beams 111T and 111R.

The illumination system 105 and light collection systems 107T and 107R are aligned to inspect various positions on the photomask 103. The entire surface of the photomask 103 is inspected by moving the one or more illumination beams 111 relative to photomask 103, and/or by moving the photomask relative to the optical system, as on a translation stage 123. In particular, the embodiment provides for measurements of phase objects at various locations on the photomask 103, and for scanning of the photomask by the inspection apparatus to assemble information useful in determining the size, location, magnitude and type of defects on the photomask. Stage 123 is omitted from some of the subsequent figures and description of embodiments to simplify the figures and description.

Reflected and transmitted light is measured with collection systems 107R and 107T, respectively. For a scanning-type system, the N pairs of beams are separated into 2 N individual beams, and the light is delivered to the appropriate detectors 121T" and 121R", where properties of the beams are measured and signals 111s" are generated. For a projector-type system, collection system 107T' includes objective 129' and separation/imaging detector 131'. In reference to FIGS. 1A–1C, the computer control system 109 controls, measures or determines the position at which photomask 103 is being inspected. In reference to FIG. 1A, positional information and signals 111s are assembled in data analysis system 125 and analyzed to produce positional information about the phase objects on photomask 103.

In reference to FIG. 1A, an autofocus system 106 intercepts light that is reflected from the photomask, and produces a signal that is provided to focus modifying optics within illumination system 105 for maintaining the focused beam 111 in proper relation to the photomask 103 by controlling the focus of the appropriate objective (117b" or 129' for the examples of FIGS. 1B and 1C, respectively). The intercepted light can either be supplied from the autofocus system 106, or can be light that is reflected from the photomask 103 during the inspection process. The focus modifying optics could be one of several arrangements, including but not limited to an objective lens that can be moved. In addition, the autofocus system 106 can also be positioned to intercept and provide signals from the incident illumination beam 11. Alternatively, the physical location of the autofocus system 106 can be incorporated into the illumination system 105 or reflected light collection system 107R.

For automated inspection of a photomask 103, it is useful to provide for scanning of the photomask by the illumination beam 111. Methods for scanning include but are not limited to: moving the photomask 103 relative to illumination beam 111; moving the illumination beam relative to the photomask; and simultaneously producing multiple inspection beams focused to different photomask locations. Thus the computer control system 109 can allow for inspection of different positions on the photomask 103 by moving the photomask in directions parallel to the face of the photomask by controlling X-Y translation stage 123, and by controlling the scanning of the illumination source beam 116" along directions perpendicular to its direction of propagation using acoustic-optic devices. In addition, multiple beams may be provided by including gratings or other devices within illumination system 105 for producing multiple beams from a single beam. These methods and devices, taken individually or in combination, can be used to inspect the photomask 103.

Among the alternative embodiments of the present invention are a defocused die-to-database (D:DB) inspection system and a multiply focused implementation. In a multiply focused implementation, pairs of differently focused beams 111 are used to inspect the photomask 102. In particular, the illumination beams 111 are provided as N pairs of beams that are differently focused onto the same approximate position on the photomask 103. Thus for example, if N=1 then the illumination beams 111 comprises one pair of beams individually focused near the same spot on the photomask. The foci are, for example, just short of and just beyond the surface of the photomask. In one alternative embodiment, the illumination system 105 provides the two beams simultaneously, while in another alternative embodiment, the two beams are provided sequentially. In this alternative embodiment, the difference inducing optics 117" is removed, so that only one illumination beam is produced at a time. The illumination beam is focused short of the mask. After one or more image swaths across the mask, the illumination beam is focused just beyond the surface of the mask. The image signals obtained during the two swaths or scans are then aligned in position and processed in the same manner as that described herein for the embodiment where two or more images are obtained simultaneously using two or more illumination beams at the same time; such and other variations are within the scope of the invention. Thus, in the preferred embodiment where two or more images are obtained simultaneously, the two or more images need not be aligned in position, so that such embodiment is more advantageous.

For example, where N is 3, and illumination beams 111 are 3 pairs of illumination beams, or 6 beams in total. Each pair is focused to a different spot on photomask 103, producing 6 modified illumination beams. The illumination beams 111 are preferably provided as scanning beams for inspection of many positions on the photomask 103.

In a D:DB system, the photomask 103 is inspected with a beam having a particular amount of defocus. A database of expected signals or combinations of signals known to be without defects (e.g. generated using an exemplary photomask) is generated or otherwise provided corresponding to locations for the particular photomask 103 under inspection at the amount of defocus, before inspection of such photomask. During or after inspection the inspected signals 111s from the photomask 103 are compared against the predetermined database of expected signals. In this way the presence or absence of defects are determined from a defocused measurement or set of measurements at a particular amount of defocus. It will be obvious to one skilled in the art that many of the subsequently described embodiments can be modified to function as a D:DB system by providing single illumination beams.

Specific Embodiments

The present invention relates to methods and systems for optical inspection. Two general embodiments that will be discussed in greater detail are focus-based systems and Zernike-based systems. In the focus-based system, multiple illumination beams are differently focused in the vicinity of the photomask. In Zernike-based systems, an objective and specially constructed Zernike plate cooperate to either illuminate the mask with a pair of beams that are orthogonally polarized and have +/−90 degree complementary Zernike point spread functions, or to interrogate a uniformly illuminated photomask with such a combination of elements. For both focus-based and Zernike-based systems, alternative embodiments include, but are not limited to scanner-type and projection-type inspection devices. Scanner-type systems are used to inspect photomasks by gathering data point-wise, while projector-type systems inspect larger areas, gathering data along lines or areas using multipoint array detectors. Data analysis of collected modified illumination beams is similar for both the scanner-type and projector-type architectures. Additional embodiments provide for database rendering, in which one or more measurements are compared against expected values from known photomask structure.

It would be understood by those skilled in the art that the specific components and combination thereof are for illustrative purposes only, and are in no way meant to limit the scope of the claims. Thus there are many configurations of optical, electro-optical and mechanical components that can be used singly and in combination to generate focused light beams in the vicinity of a photomask and measure individual beams after being modified by the photomask. Specifically, for example: scanning beams can be generated from a single light beam using acousto-optics; coaxial, differently focused beams can be generated from a single beam based on polarization effects, such as with birefringent lens, based on diffraction effects, such as with a multifocal zone plate, or by sequentially moving the focus relative to the photomask; beams can be separated according to their polarization or spatial separation; and data can be gathered at single points or through imaging.

Detectors for use with the invention include, but are not limited to point, one-dimensional and two-dimensional CCD array detectors, or any detectors that are sensitive to light at the wavelength(s) of the illumination source. Lenses shown in specific embodiments may be replaced with combinations of lenses, appropriate mirrors or combinations of lenses and mirrors. Mirrors may be included into the various optical paths to reduce the physical size of the apparatus or to avoid other apparatus components. Other polarizing elements may be included to provide the necessary system sensitivity. Also, the pairs of images obtained for inspecting photomasks can be collected by various combinations of detectors and illumination scanning, and can be collected with one detector per focal position, by projecting the images side-by-side on array detectors, or by modifying an array detector to interleave the images. In addition, components such as autofocus systems can be placed in the incident beam or in a modified beam, or in some circumstances can be left out of the apparatus.

Optical Inspection of Photomasks

Optical inspection details are provided in greater detail in FIG. 2 for a projector-type system, which shows a side sectional view of the inspection apparatus as it is applied to a Levinson-type PSM. FIG. 2 shows multiply focused beams 111-1 and 111-2 impinging on photomask 103 to facilitate an understanding of focus-based embodiments. In the projector-type system, the imaging optics gathers modified beams, preferably with a resolution of less than one phase shifter. The configuration depicted in this figure is not meant to limit the scope of the present invention, which includes embodiments that illuminate with single illumination beams.

The photomask 103 of FIG. 2 is provided for convenience in furthering the discussion of the present invention, and is not meant to limit the scope of the present invention to any particular object containing phase-modifying features.

As shown in FIG. 2, the one pair of illumination beams 111 comprises a first beam 111-1 and a second beam 111-2 that are preferably coaxial along a propagation path 111a. As described previously, it is within the scope of the present invention that individual ones of the pair of illumination beams 111 may be provided sequentially or simultaneously to photomask 103, and thus the same beam may be positioned sequentially at different foci at positions 111-1 and 111-2 as seen in FIG. 2. In addition, scanning-type systems may have multiple scanning pairs (N>1). Note that in Zernike-based systems the two beams 111 differ in point spread function and have essentially the same focus and the two Zernike-based illumination beams essentially overlap, where again two beams may be employed simultaneously, or a single beam may be used sequentially.

The propagation path 111a is approximately perpendicular to the photomask 103. For focus-based systems the illumination beams 111-1 and 111-2 are focused to different focal distances along the propagation path, specifically at foci 111-1F and 111-2F, respectively, while for Zernike-based systems the foci 111-1F and 111-2F are preferably approximately coincident. In general, the foci should be near or about objects on the photomask 103 to be inspected. For focus-based systems the foci are situated on either side of phase objects on the front surface of photomask 103. Illumination beam(s) at positions 111-1 and 111-2 are modified by their interaction with the photomask 103 and emerge as modified illumination beams 111-1T and 111-2T, respectively.

The photomask 103 is a Levinson-type PSM comprised of a substrate 201 having a flat surface 205 and a patterned surface 207. Substrate 201 is usually a transparent material, such as quartz. The patterned surface 207 includes opaque regions 209, usually a metal, such as chrome, that can be arranged as stripes in a two-dimensional grid pattern. Patterned surface 207 areas that are not covered by opaque regions 209 include a plurality of clear area phase shifters 211 and a plurality of etched area phase shifters 213. Phase shifters 211 and 213 induce phase shift in illumination beam(s) 111-1 and 111-2 according to the thickness of photomask 103 and the optical properties of the substrate 201. As one example of a photomask 103, chrome may be deposited along the front surface 207 as strips 300 nm wide, with 300 nm square phase shifters between the strips. The phase shifters may have the same thickness as the substrate 203, such as clear area phase shifters 211, or may have material removed from the substrate, such as etched area phase shifters 213, or may have radiation transmitting material added to the substrate (not shown). Phase objects include but are not limited to precise variations of the thickness of a transparent mask, and the controlled attenuation of a small percentage of the incident light at a given wavelength. PSMs usually contain phase objects that shift the phase of incident light by specified, discrete phases, such as 0 and 180 degrees, or 0, 60, 120, and 180 degrees.

The illumination beam(s) 111 are provided for inspection of the photomask 103, and in particular to determine the presence of defects within shifters. The illumination beam impinges on patterned surface 207, and is transmitted through to flat surface 205. The foci 111-1F and 111-2F are generally positioned near the phase object of interest—namely phase shifter 213. For focus-based systems, either of the foci 111-1F or 111-2F may be located at a position that focuses to the photomask 103 (i.e. focus at front surface of photomask), or they may both be at a defocused location, as shown in FIG. 2. The response of the various detectors will depend on the relative location of the phase shifters 213 and the foci 111-1F and 111-2F, with good results expected but not limited to foci on either side of the shifters. For Zernike-based systems, the foci 111-1F and 111-2F are preferably located near the position that focuses to the photomask.

As an alternative embodiment, the inspection of the photomask 103 may proceed by probing the wafer from the flat surface 205. For these embodiments, the photomask 103 of FIG. 2 is reversed, with the illumination beam first encountering flat surface 205 as a front surface.

The transmitted and thus modified illumination beams 111-1T and 111-2T will be modified by the combined phase and amplitude variations of the several adjacent phase shifters within the path of the illumination beams 11. The variation of intensity of the modified illumination beams 111-1T and 111-2T in a plane perpendicular to propagation path 111$a$ will thus include the diffraction by the opaque material 209 and the effects of phase shifters 211 and 213. In addition to inspecting the transmitted light, reflected light also provides useful information on the photomask 103. The reflected light (not shown) propagates back towards the illumination source, counter-propagating along propagation path 111$a$. Several of the embodiments illustrate the collection and analysis of reflected light.

Focus-based Embodiments

A more specific embodiment of the present invention will provide a greater understanding of the various inventive aspects and advantages of the present invention. The following discussion illustrates the illumination and interaction of illuminated light with a Levenson-type PSM. The illumination and collection optics are not presented in this particular discussion. For purposes of discussion, it will be assumed that a projector-type system is being used, and that the modified illumination beams are being imaged with a resolution such that the point spread function of objective is much less than the lateral extent of the phase shifted region shifter size. FIGS. 18A–18C illustrate an embodiment of the present invention for a focus-based optical system, where FIG. 18A is a sectional view of the Levenson-type PSM, or photomask, 103 with a phase defect 1801, and FIG. 18B is a plot of the modified light intensity from the two, differently focused illumination beams 111-1T (the "+ defocused" beam) and 111-2T (the "− defocused" beam). The rays are those which, when followed forwards through the objective of the optical system, will be collected by individual optical detector elements. The + and − defocused beams are defocused by the objective by $\pm\lambda/NA^2$, respectively, where $\lambda$ is the illumination wavelength and NA is the numerical aperture of the objective. As shown in FIG. 18, two illumination beams 111-1 and 111-2 having foci at 111-1F and 111-2F, respectively, are transmitted through photomask 103, resulting in transmitted illumination beams 111-1T and 111-2T, respectively. The photomask 103 includes a series of phase objects, or pixels, including clear area phase shifters 211, also referred to as 0 degree phase shifters, and etched area phase shifters 213, also referred to as 180 degree phase shifters. For illustrative purposes, a phase defect 1801 has been placed at the bottom of one of the phase shifters. The photomask 103 also includes opaque regions 209 between the phase shifters.

The spatial distribution of intensity for the various beams is shown in FIG. 18B. The individual traces 1803–1811 are shifted vertically so that they can be seen separately. The actual values of each curve is approximately zero at X=0 pixels. The intensity profile 1807 is the intensity of the illumination beams 111-1 and 111-2 at their respective foci. For the purposes of this illustration of the present invention, an Airy function spanning approximately 5 pixels was chosen. As shown in FIG. 18A, the illuminated area includes 0 degree phase shifters 211, 180 degree phase shifters 213, opaque regions 209, and a phase defect 1801 in one of the phase shifters. The intensity distribution of the transmitted beams 111-1T and 111-2T is also shown in FIG. 18B. Intensity profiles 1803 and 1805 are, respectively, the real and imaginary parts of the + defocused beam 111-1T. Intensity profiles 1809 and 1811 are, respectively, the real and imaginary parts of the − defocused beam 111-2T. The real parts of the two beams (1803 and 1809) have approximately the same intensity distribution, while the imaginary parts of the two beams (1805 and 1811) have different signs. Thus subtracting the total intensity of the two beams tends to subtract out the modifications to the illumination beams by amplitude objects and highlight modifications due to phase objects. As will be shown subsequently in the DATA ANALYSIS section, the signals can be examined to determine much useful information about the photomask and about the phase defect in particular.

Optical Design Considerations for Focus-Based Systems

Due to the reciprocity principle, scanning-type imaging systems of the present invention are optically equivalent to partially coherent projector type imaging systems, e.g. a microscope. One approach to understand the response of focus-based systems of the present invention to phase shift objects is through consideration of the transfer function of a partially coherent imaging system with defocused light (see, for example, S&W referenced above). The analysis of the present invention is simplified to one spatial and one spatial frequency coordinate. For a detailed analysis of a one-dimensional inspection system, please see S&W.

Consider an object having a transmittance t(x) that is placed with its surface perpendicular to the direction of light travel within an optical system. The transmittance t(x) can be a real number, representing an amplitude object, an imaginary number, representing a phase object, or a complex number combining both phase and amplitude objects. The transfer function C(m,p) can be used to calculate the intensity of light I(x) in an image plane of an imaging system. In particular, the transfer function C(m,p) depends on the light source, detection optics and other optical elements of the optical system, where m and p denote spatial frequencies in the same, one-dimensional, direction. In the approximation of thin masks, i.e., ignoring surface relief effects as well as vector and rigorous diffraction effects, the image intensity may be computed from the Fourier transform of the object transmittance and transfer function as follows:

$$I(x) = \int_{-\infty}^{\infty}\int_{-\infty}^{\infty}\int_{object} C(m,p)T(m)\overline{T(p)}\exp(2\pi i(m-p)x)\,dx\,dm\,dp$$

where x is the image plane coordinate, and the bar over a function represents the complex conjugate. The integration is performed over all spatial frequencies and over the extent of the object. T(m) is the Fourier transform of the object transmittance given by:

$$T(m) = \int_{-\infty}^{\infty} t(x)\exp(-2\pi i m x) dx$$

$C^+(m,p)$ will be used to denote the transfer function when the focus is beyond the transmittance objects, such as with illumination beams 111-1, while $C^-(m,p)$ will be used to denote the transfer function when the focus is short of the transmittance objects, such as with illumination beams 111-2.

The transfer function may be approximated using Equation 5 of Sheppard and Wilson (S&W). Assuming a point source defined by $S(x)=\delta(x)$, where $\delta(x)$ is the Dirac delta function, and a large uniform detector $D(x)=1$, the transfer function can be calculated for a scanner type, partially coherent imaging system illuminated by a coherent point source. With the above-mentioned equivalence of the projector and scanner systems, the pupil function $P_1$ corresponds to the objective and the $P_2$ to the condenser. Using a defocused pupil function $P_1$ with defocus $\alpha_2=z$ according to S&W equation (23), setting the clear aperture of $P_1$ to 1 and the clear aperture to $\sigma$, and the condenser defocus to zero with M=1 yields the following pupil and transfer functions, where the bars denote complex conjugates and $\xi_1$ and $\xi'_1$ are the pupil plane coordinates of S&W, respectively. These assumptions can be used in Equation 5 of S&W to yield the transfer function simplified for objects varying in one-dimension:

$$c(m, p) := \int_{\max(-1,-\lambda \cdot f \cdot p + \lambda \cdot f \cdot m - 1)}^{1} \lambda \cdot f \cdot \Phi(1 - \lambda \cdot f \cdot p + \lambda \cdot f \cdot m - \xi) \cdot$$
$$\Phi(\lambda \cdot f \cdot m - \xi + \sigma) \cdot \Phi(\sigma - \lambda \cdot f \cdot m + \xi) \cdot$$
$$\exp[-i \cdot [z \cdot (\lambda \cdot f \cdot p - \lambda \cdot f \cdot m + \xi)^2]] \cdot \exp(i \cdot z \cdot \xi^2) d\xi$$

where $\Phi(x)$ is the Heaviside step function. Differently focused transfer functions corresponding to +z and −z defocus will be denoted $C^+(m,p)$ and $C^-(m,p)$, respectively.

The image intensity $I^+(x)$ of an arbitrary object $t(x)$ with corresponding spatial frequency distribution $T(m)$ according to S&W equation (1) is now given as:

$$I\_plus(x) := \int_{-\infty}^{\infty}\int_{-\infty}^{\infty}\int_{\max(-1,-\lambda \cdot f \cdot p + \lambda \cdot f \cdot m - 1)}^{1} \lambda \cdot f \cdot \Phi(1 - \lambda \cdot f \cdot p + \lambda\lambda \cdot$$
$$f \cdot m - \xi) \cdot \Phi(\lambda \cdot f \cdot m - \xi + \sigma) \cdot \Phi(\sigma - \lambda \cdot f \cdot m + \xi) \cdot$$
$$\exp(i \cdot z \cdot \xi^2) \cdot \exp[-i \cdot z \cdot (\lambda \cdot f \cdot p - \cdot f \cdot m + \xi)^2] \cdot$$
$$T(m) \cdot \overline{T(p)} \cdot \exp[2 \cdot \pi \cdot i \cdot (m - p)] \cdot x d\xi d m d p$$

In addition to the symmetry properties of the transfer function listed in S&W equations (7) and (8), i.e. real sources and detector intensities and centered pupils, $$C(m,p) := \overline{C(p,m)} \quad S\&W \quad (7)$$

$$C(-m,-p) := C(m,p) \quad S\&W \quad (8)$$

The differently focused transfer functions also fulfill the symmetry condition:

$$C\_plus(m,p) := \overline{C\_minus(m,p)}$$

The +/− defocus difference image intensity $DI(x)=I^+(x)-I^-(x)$ for an arbitrary phase and amplitude object $T(m)$ can now be obtained as follows:

$$I\_plus(x) - I\_minus(x) := \int_{-\infty}^{\infty}\int_{-\infty}^{\infty}\int_{\max(-1,-\lambda \cdot f \cdot p + \lambda \cdot f \cdot m - 1)}^{1}$$
$$(C\_plus(m, p) - C\_minus(m, p)) \cdot T(m) \cdot$$
$$\overline{T(p)} \cdot \exp[2 \cdot \pi \cdot i \cdot (m - p)] \cdot x d\xi d m d p$$

The following general results follow from the previous discussion of a simplified analysis of the present invention. If the transmittance is real (an "amplitude object"), then T is real (and equal to its complex conjugate), and $DI(x)$ is seen to be zero. Thus, in the thin mask approximation, a perfectly flat quartz plate with an arbitrary chrome pattern imaged in transmitted light will produce a $DI(x)$ that is zero, independent of position x. If the transmittance is imaginary (a "phase object"), then T is complex and $DI(x)$ is a maximum. As an example, an imaginary region on an otherwise real object, i.e. a 90-degree phase shifted region on a quartz plate imaged in transmission, will produce maximum difference image intensity.

The comparison of differently focused modified illumination beams will selectively produce intensity signals according to the imaginary part of the complex phase and amplitude distribution of an object. In particular, 0 degree (non-shifted) and 180 degree shifted regions and chrome patterns will be suppressed as real objects and produce no DI signal. Only the phase features different from 0 and 180 degrees will appear in the difference image. The present invention thus can function as an optical phase defect detector. The detection of modified light and analysis of signals provides for the detection of variations of phase across the sampling area, even in the presence of opaque objects. The detection is sensitive both to variations that occur between imaged phase objects and to slight variations due to defects.

The above relations can also be applied to two-dimensional objects with similar results. With objects having surface relief, slight differences are expected due to vector diffraction and other effects. This discussion has been meant to highlight the advantageous features of the differently focused imaging system to be very sensitive and to allow measurement of phase objects according to differences in intensity. In addition, the sensitivity of the variable $DI(x)$ to phase objects is not meant to limit the scope of analysis techniques according to the present invention. In particular, the intensities of signals resulting from the plus and minus modified beams may be combined in other arithmetic formulations, or signals representative of the beams may be compared graphically, as one signal against the second signal, or some combination of signals against other combinations of signals. The discussion of the following features is meant to provide some guidelines by which focus-based optical inspection systems can be constructed, and is not meant to limit the scope of the present invention. The modulation of light intensity will depend, among other parameters, on the amount of defocusing of the illumination beams. Thus for example, the difference between the focal distances is preferably less than or approximately equal to $4\lambda/NA^2$, where $\lambda$ is the wavelength of the illumination beams and NA is the numerical aperture of the objective of the optical system. The position of the focus is preferably close to the location of the phase objects. The pair of foci is preferably, though not necessarily, on either side of the phase objects. In addition, having illumination beams that are nearly circularly polarized at the surface can reduce patterning effects. This is achieved by introducing a quarter-wave plate at the pupil plane prior to illuminating the mask. A second quarter-wave plate can be used to convert the light that has been modified by the mask back to linear polarization.

To achieve high sensitivity of the inspection system, the wavelength of the illumination beam should be selected to produce large signals for objects of interest and low signals for background objects. Specifically, these requirements are met if the design wavelength of a 0–180 degree Levinson-type PSM is the same as the wavelength of the illumination beam(s). The design wavelength is that employed by a stepper lithographic device. In this case only areas producing phase shift different from 0 and 180 degrees will produce a non-zero difference intensity, with maximum at 90 degrees. In addition, signal processing in this case is simplified.

Focus-based, Scanner-type Systems

Focus-based systems generate multiple signals by differences in the focus of the system objective. A first embodiment of the present invention is shown in FIGS. 3A and 3B for a focused-based, transmitted and reflected light, scanning-type photomask inspection system 101". In this embodiment, N=1, and there is one pair of illumination beams 111". The first embodiment produces two differently-focused and differently-polarized beams, collects light from the beams that have been modified by a photomask, separates the modified beams according to their respective polarizations, and then collects each of the modified beams onto a detector. The system generates pairs of signals at the same approximate photomask location, and inspects a photomask by scanning the illumination beams and moving the photomask.

The inspection system 101" includes an illumination system 105" comprising the illumination source 115" and the difference-inducing and focusing optics 117", the autofocus system 106, and a transmitted-light collection system 107T" and a reflected-light collections system 107R". The illumination source 115" includes a light source (not shown) for producing a linearly polarized beam 300, an acousto-optic modulator 301 for focusing and scanning the beam (as indicated by the double sided arrows), and a lens 303 for collimating the beams. The light source may be a laser, preferably a continuous wave laser (e.g. one providing ultraviolet light), or other suitable sources known to those skilled in the art. The output of the illumination source 115" is a nearly collimated, linearly polarized scanning beam 116". The difference inducing and focusing optics 117" generate illumination beams which are focused to different depths within the photomask 103. Specifically, difference-inducing and focusing optics 117" consist of divergence-inducing optical element, specifically a birefringent lens 305, a quarter-wave plate 313 and an objective 315. The birefringent lens 305 is oriented with the ordinary and extraordinary axes at 45 degrees to the polarization of scanning beams 116". Alternatively, a birefringent zone plate having positive and negative powers of the even and odd zones may be used. The birefringent lens 305 produces two beams of different polarizations and different divergence. The scanning beam 116" is thus transmitted through the birefringent lens 305, producing coaxial beams 111-1" and 111-2" of different divergences. The quarter wave plate 313 produces polarizations at the photomask 103 that have been shown to produce useful results—specifically left and right circular polarizations. This is useful because the orientation of any features or pattern on the photomask relative to the beam 116" does not affect the measurement. The objective 315 focuses beams 111-1" and 111-2", which now has left and right circular polarizations, to foci 111-1F" and 111-2F", respectively, as illustrated in more detail in FIG. 2.

In addition to the divergence and focusing optics 117", the pair of illumination beams 111" is also transmitted through other optics. Included in the first embodiment are: an autofocus system 106 comprised of a polarizing beam splitter 307 and autofocus optics and electronics 323 for keeping the differently focused beams centered on photomask 103; a polarizing beam splitter 309; and relay optics 311 for changing the magnification of the optical system or the inspection location.

In the first embodiment, the illumination beams 111-1" and 111-2" are transmitted through, and modified by, the photomask 103, producing transmitted illumination beams 111-1T" and 111-2T". The collection system 107T" collects the transmitted light, separates the beams according to their focal position, and generates signals proportional to each of the transmitted beams. Separation is accomplished by: 1) reintroducing the polarization difference between the two separately focused beams, and 2) passing the light through a polarizing beam splitter to spatially separate the beams. Specifically, the transmitted light collection system 107T" includes an anamorphic collection lens 317, a quarter-wave plate 319 and transmitted-light (TL) detection system 321T that produces signals 111s". The TL detection system 321T includes separation optics 119T" and detectors 121T". The lens 317 collects both of the modified beams 111T" (i.e. 111-1T" and 111-2T"); the quarter-wave plate 319 undoes the effect of quarter-wave plate 313 and converts both beams to linearly polarized ones and re-establishes a polarization difference between the two beams.

The polarization difference between the differently focused beams is used as the basis for separation of the beams in the TL detection system. The TL detection system 321T, as shown in FIG. 3B, includes an aperture stop 325, a polarization beam splitter 327, and two pair of lenses and detectors: a first cylindrical lens 329 for focusing beam 111-2T" onto detector 331, and a second cylindrical lens 333 for focusing beam 111-1T" onto detector 335. The aperture stop 325, which has a pupil plane to limit the coherence to 0.5, transmits both of the modified beams 111T" before they are individually diverted according to their respective polarizations by the beam splitter 327. Both detectors 331 and 335 produce signals 111s" (as shown in FIG. 1B) according to the intensities of beams 111-2T" and 111-1T", respectively.

Although the transmitted and reflected light passes through different optical components, the separation and detection schemes are similar. Thus the transmitted light passes sequentially through the collection lens 317, the quarter-wave plate 319 and the transmitted-light (TL) detection system 321T, while the reflected light passes sequentially through the objective 315, the quarter-wave plate 313, the polarizing beam splitter 309, and a RL detection system 321R. The RL detection system 321R and TL detection system 321T contain the same components. It is understood that for obtaining useful signals may be desirable that some of the components have slightly different optical characteristics. In addition, alternative embodiments may perform the functions of the claimed invention with equivalent components.

Detectors 331 and 335 are chosen to produce high speed signals indicative of the intensity of light sensed thereby. Examples of detectors are ultraviolet sensitive silicon photodiodes sized for high bandwidth. A useful measurement of the optical properties of photomask 103 results from comparing signals from differently focused beams at the same location. One method of producing such signals in the first embodiment is to subtract the signal of detector 331 from that of detector 335. The subtraction of signals can occur in a data analysis computer 125, through circuitry (not shown) connected to the detectors 331 and 335, or through other techniques known in the art of signal processing. A more detailed analysis of the use of detector signals to produce an indication of phase defects will be presented subsequently. By collecting signals during the scanning of the beam using an acousto-optic modulator (not shown in FIG. 1B) in source 115" and movement of the photomask 103 using the translation stage 123, a two-dimensional assembly of data corresponding to photomask 103 positions can be assembled to inspect the entire photomask surface.

A second embodiment of the present invention in the form of a focus-based, scanning-type architecture is presented in FIGS. 4A and 4B that may be used to simultaneously inspect three points on a photomask, that is where N is 3. The principle of operation of the second embodiment is similar to that of the first embodiment with polarization effects used to produce focused beams that are then separated according to their polarization. The embodiments differ in that the second embodiment includes the generation of multiple pairs of differently focused and differently polarized beams. The multiple pairs inspect a photomask at the multiple, scanning points (as indicated by the double sided arrows), and the separation and detection systems produce signals for each of the multiple pairs of modified beams. The configuration is applicable in general to both transmitted and reflected light.

The inspection system 101" has many of the same components as the first embodiment for inspection using transmitted light. Additional components are used to produce, separate and detect the multiple pairs of illumination beams 111". Specifically, the illumination source 115" includes a grating 401 that produces multiple, nearly collimated, scanning beams 116". The grating 401 is configured to produce 3 output beams for each input beam 300. Suitable grating or grating-like elements include holograms or phase gratings with high +/− first order diffraction efficiency. Scanning beams can be alternatively generated by producing one pair of differently focused beams, and then passing the pair through a grating to produce multiple pairs of focused beams.

The scanning beam 116" traverses the birefringent lens 305, producing three pairs of coaxial beams of different divergences so that the three pairs are separated laterally. The quarter wave plate 313 produces left handed and right handed circular polarizations of the illumination beams 111" at the photomask 103. The objective 315 takes the pairs of beams 111a-1, 111a-2; 111b-1, 111b-2; 111c-1, 111c-2 and focuses them to foci 111a-1F" and 111a-2F"; 111b-1F" and 111b-2F"; and 111c-1F" and 111c-2F" respectively, as illustrated in FIGS. 2 and 4B. In particular, foci 111a-1F", 111b-1F", and 111c-1F" are focused at the same approximate focal plane, as are 111a-2F", 111b-2F", and 111c-2F". As in the first embodiment, the autofocus system 106 is used to keep the differently focused beams centered on photomask 103, and the relay optics 311 are used to changing the magnification of the optical system or the inspection location are also included.

The three pairs of illumination beams 111" are transmitted through, and modified by, the photomask 103, producing three pairs of modified illumination beams 111T". The transmitted light collection system 107T" is adapted to separate and produce signals from each of the six modified illumination beams, and includes a collection lens 317, a quarter-wave plate 319 and transmitted-light (TL) detection system 421. The lens 317 collects all the modified beams 111T" and the quarter-wave plate 319 re-establishes a polarization difference between the beams in each pair in the same manner as that described above. The TL detection system 421, as shown in FIG. 4B, includes separation optics 119T" and detectors 121T". The separation optics 119T" and detectors 121T" are comprised of an aperture stop 425, a polarization beam splitter 427, a first pair of lenses and detectors: a first anamorphic cylindrical lens 429 for focusing beams 111a-2T", 111b-2T", and 111c-2T" onto detectors 431a–c, respectively, and a second pair of lenses and detectors: a second anamorphic cylindrical lens 433 for focusing beams 111a-1T", 111b-1T", and 111c-1T" onto detectors 435a–c, respectively. The aperture stop 425, which has a pupil plane to limit the coherence to 0.5, transmits both of the modified beams 111T" before they are individually diverted according to their respective polarizations by the beam splitter 427. Both detectors 431 and 435 produce signals 111s" (as shown in FIG. 1B) according to the intensity of the respective beams 111T".

Detectors 431 and 435 can either be individual detectors, similar to the first embodiment detectors 331 and 335, or can be array detectors. Examples of detectors are high bandwidth ultraviolet-sensitive silicon photodiodes. Alternatively, transmitted light collection systems 107T" may in general include optics to fold the various optical paths and present the individual modified beams 111T" onto a two-dimensional array detector. In addition, fewer or more than three measurements could be obtained simultaneously by alternatively using a grating 401 that produces fewer or more than three beams and the appropriate detectors to individually measure the modified beams.

A third embodiment of a scanning-type, focus-based implementation of the present invention is presented in FIGS. 5A–C, which shows a transmitted and reflected light scanner-type inspection system utilizing interference effects and spatial filtering to produce one pair (N=1) of differently-focused beams. Specifically, this embodiment produces two differently focused beams, collects light from the beams that has been modified by a photomask, refocuses the modified beams onto a spatial filter, allowing for separation based on the inspection focal position, and then collects each of the modified beams on a detector. The system generates pairs of signals at the same approximate photomask location, one pair at a time, and inspects a photomask by scanning the illumination beams and moving the photomask.

The inspection system 101" includes the illumination source 115", the difference inducing and focusing optics 117", and a transmitted-light collection system 107T" and a reflected-light collections system 107R". An autofocus system is not shown in this embodiment, but can be incorporated either before or after the photomask 103. The illumination source 115" includes a light source (not shown) for producing a beam 300, the acousto-optic modulator 301, and the lens 303. As before, the light source may be a laser or other suitable sources known to those skilled in the art. The output of the illumination source 115" is one, nearly collimated, scanning beam 116".

The difference inducing and focusing optics 117" includes an optical element 505, a system pupil 508, the quarter-wave plate 313, and the objective 315. The A suitable optical element 505 that produces more than one beam with different foci includes a multifocal zone plate as described by Cohen in U.S. Pat. Nos. 5,144,483; 4,995,714 and 4,338,005, which are incorporated herein by reference in their entireties. The scanning beam 116" is transmitted through the multifocal zone plate 505 and system pupil 508, producing coaxial beams 111-1" and 111-2" of different divergences. The quarter wave plate 313 produces the previously noted useful polarizations at the photomask 103. In addition to the difference inducing and focusing optics 117", the pair of illumination beams 111" is also transmitted through other optics. Included in this embodiment are: a polarizing beam splitter 509; and relay optics 311 for changing the magnification of the optical system or the inspection location.

The collection system 107T" collects the transmitted light, separates the beams according to their focal position, and generates signals proportional to each of the transmitted beams. Separation is accomplished by refocusing the pair of modified illumination beams onto a spatial filter, which individually directs the modified beams to different detector elements. Specifically, the transmitted light collection system 107T" includes a collection lens 317, a quarter-wave plate 319 and transmitted-light (TL) detection system 521T that produces signals 111s". The TL detection system 521T includes separation optics 119T" and detectors 121T". The lens 317 collects both of the modified beams 111T" and the quarter-wave plate 319 re-establishes a polarization difference between the two beams.

The difference in focal positions is used as the basis for separation of the beams in the TL detection system. The TL detection system 521T, as shown in FIG. 5B, includes an aperture stop 525, a spatial filter 527, a cylindrical lens 529 for focusing beams 111-1T" and 111-2T" onto a detector 531 having two elements, 531a and 531b. The aperture stop 525, which has a pupil plane to limit the coherence to 0.5, transmits both of the modified beams 111T" before they are individually diverted according to their respective polarizations by the spatial filter 527. The spatial filter 527 deflects beams 111-1T" and 111-2T" side-by-side, allowing the single detector 531 with the two elements 531a and 531b to detect the two signals.

The spatial filter 527 as shown in FIG. 5C is comprised of a transparent plate 535, of a material such as quartz, with reflective spots 537 that are a material, such as a metal, deposited on opposite sides of the plate. The spots 537 are offset according to focal distance of the transmitted beams 111T" after passing through lens 517 and the thickness of plate 535. With the spatial filter 537 properly aligned near the focal position of the two beams, the paths of the individual illumination beams can be laterally offset for focusing by cylindrical lens 529 onto detector 531.

The RL detection system 521R includes the components of 521T, with optical characteristics chosen to maximize the signals from reflected light. In addition, the RL detection system 521R has detectors that produce signals in a manner analogous to those of the TL detection system 521T. Detector 531 is chosen to produce useful indications of the intensity of light, and can be either an array detector with two or more detector elements, or could be two individual detectors.

A fourth embodiment of the present invention is presented in FIGS. 6A–C, which adds multiple scanning spots (N>1) to the third embodiment. Specifically, this embodiment produces N=3 pairs of differently focused beams, collects light from the beams that has been modified by a photomask, refocuses the modified beams onto a spatial filter, allowing for separation based on the inspection focal position, and then collects each of the modified beams on a detector. The system generates three pairs of signals at the same approximate photomask location, and inspects a photomask by scanning the illumination beams and moving the photomask. The ability to inspect multiple locations greatly shortens the inspection time.

The inspection system 101" has many of the same components as the third embodiment for inspection using transmitted and reflected light. Additional components are used to produce, separate and detect the multiple pairs of illumination beams 111". Specifically, the illumination source 115" includes a grating 401 that produces multiple, nearly collimated, scanning beams 116". The grating 401 is configured to produce 3 output beams for each input beam 300. The 3 scanning beams 116" traverse the difference-inducing and focusing optics 117", which consist of the multifocal zone plate 505 to produce two diverging beams for each of the three scanning beams, the system pupil 508, the quarter-wave plate 313 to cause the beams to have circular polarizations, and the objective 315 for focusing each of the illumination beams 111". In particular, the objective 315 takes the three pairs of beams, and focuses them to foci 111a-1F" and 111a-2F", 111b-1F" and 111b-2F", and 111c-1F" and 111c-2F" respectively, as shown in FIGS. 2 and 6A. Foci 111a-1F", 111b-1F", and 111c-1F" are focused at the same approximate focal plane, as are 111a-2F", 111b-2F", and 111c-2F".

The three pairs of illumination beams 111" are reflected from and transmitted through the photomask 103, producing three pairs of modified illumination beams 111T" and 111R", respectively. The collection system 107T" collects the transmitted light, separates the three pairs of beams according to their focal positions, and generates signals proportional to each of the transmitted beams. Separation is accomplished by refocusing the pair of modified illumination beams onto a spatial filter, which individually directs the modified beams to different detector elements. Specifically, the transmitted light collection system 107T" includes a collection lens 317, a quarter-wave plate 319 and transmitted-light (TL) detection system 621T that produces signals 111s". The TL detection system 621T includes separation optics 119T" and detectors 121T".

The difference in focal positions is used as the basis for separation of the beams in the TL detection system. The TL detection system 621T, as shown in FIG. 6B, includes an aperture stop 625, a spatial filter 627, a cylindrical lens 629 for focusing each of the 6 beams 111T" onto detector 631 having six elements D1–D6. The aperture stop 625, which has a pupil plane to limit the coherence to 0.5, transmits both of the modified beams 111T" before they are individually diverted according to their respective focal positions by the spatial filter 627. The spatial filter 627 deflects individual ones of beams 111T" side-by-side, allowing the single detector 631 with the six elements D1–D6 to determine the individual intensities and report signals 111s".

The spatial filter 627 as shown in FIG. 6C is comprised of three spatial filters 527, or their equivalent. The spatial filter 637 has reflecting spots 537 located at each of the locations of the transmitted beams 111T" as focused by lens 317. The stacking of the three spatial filters 527 allows for deflection of the six beams onto detectors D1–D6. For example, detectors D1 and D4 detect the transmitted beams 111a-1T" and 111a-2T", respectively. According to the present invention, one system for analyzing the signals would form the difference of the signals from D1 and D4 as being representative of the phase induced near the focus 111a-1F".

Detector 627 can either be individual detectors, similar to the first embodiment detectors 331, or can be array detectors. Examples of detectors are high bandwidth ultraviolet-sensitive silicon photodiodes. In addition, more than three measurements could be obtained simultaneously by alternatively using a grating 401 that produces more than three beams and the appropriate detectors to individually measure the modified beams.

Focus-based, Projector-type Systems

Projector-type, focus-based inspection systems share many of the illumination aspects of scanning-type focus-based systems. While scanning-type systems collect modified light point-by-point, projector-type systems use collection systems that image the modified light over the illuminated surface area. One difference is that since it is preferable that the objective view the side of the photomask having surface features, that the illumination beams 111″ are oriented to impinge on photomask front surface 207, while for projector-type systems it is preferred that the illumination beams 111′ impinge on photomask back surface 205. In designing the collection system it is important that while in scanning-type systems the resolution is limited by the illumination spot size, the resolution of projector-type systems depends primarily on the optical and sensor design of the collection system. In the subsequent description of the various embodiments of projector-type systems, it is understood that computer control 109 and data analysis system 125 of FIG. 1A control the inspection and data analysis process.

A fifth embodiment of the present invention is presented as a focus-based, projector-type architecture 101′ in FIG. 7. In the fifth embodiment images of modified illumination beams are collected by sequentially switching the focus of the light collection systems between two different focal positions, such as by moving the optics (illumination or collection optics) or the photomask or both. Specifically, the photomask is illuminated and a first image is collected with the objective focused to a first position, followed a second image collected with the objective focused to a second position. The fifth embodiment 101′ includes an illumination system 105′ comprising a light source (not shown) that produces a single illumination beam 111′, a quarter-wave plate 701, and a focusing lens 703 for focusing an area of the photomask 103.

The projector-type collection system 107T′ includes focusing optics, and specifically the objective lens 705, and a separation and imaging detector that includes a second quarter-wave plate 707, an imaging lens 711, and an imaging detector 713. Multiple focused images are obtained by switching the focus of objective 705 between two foci. Also included in the first projector-type inspection system is an autofocus system 106 that includes a polarizing beam splitter 709 positioned to divert light towards the photomask, for achieving focusing through an internal light source (not shown).

The imaging detector 713 can be a linear or two-dimensional array detector that has a good response to the wavelength of the single illumination beam 111′. Preferably, the imaging detector 713 is a time delay integration (TDI) detector. A TDI detector is a two-dimensional CCD detector where the collected signal is shifted along the rows at a controllable shift speed. The optical system is configured to scan the mask in time with the shift speed, thus allowing a two-dimensional image to be acquired. After the image is acquired with the objective 705 at one focal position, the focus of the objective is shifted to a different focal position at which the data acquisition is repeated. Specifically, the autofocus 106 and computer control 109 adjust the focus of the objective 705 to a first focus, for example focus 111-1F′ of FIG. 2, by manipulation of objective 705, and a first image of transmitted light 111T′ is collected by imaging array 712 into data analysis system 125. The autofocus 106 then adjusts the objective 705 to a second focus, for example focus 111-2F′ of FIG. 2, and a second image is collected by imaging array 712 into data analysis system 125. In this way the data analysis system 125 can compile point-by-point two-dimensional intensity data for both beams.

A sixth embodiment of the present invention is shown in FIGS. 8A and 8B as a focus-based, projection-type system. Illumination system 105′ includes a polarization modulator 801, as well as the quarter-wave plate 701 and the focusing lens 703. The polarization modulator 801 is for example, a KD*P EO-crystal that switches at the line rate of the TDI detector under the control of computer 109 of FIG. 1A. Illumination beams leaving polarization modulator 801 have different polarizations and different divergences. The two single illumination beams 111′ are thus electronically switched between the two polarizations, as shown by the curved arrows in FIG. 8A. The collection system 107T′ includes focusing optics 129′ (FIG. 1C) specifically a birefringent objective 803, and separation and imaging detector 131′ (FIG. 1C) including the quarter-wave plate 707, polarizing beam splitter 709, focusing lens 711, and a detector 804, as will be described subsequently. Beam splitter 709 separates the two beams by means of their different polarizations. The birefringent lens 803 is positioned to bring the differently polarized beams 111T′ onto the same approximate position on imaging detector 713.

The detector 804 is an imaging detector that collects the two beams 111T′. In general detectors 804 can be two detectors, such as a linear or two-dimensional CCD detector, chosen to have a good response to the wavelength of the single illumination beam 111′. Preferably, the imaging detector 804 is one time delay and integration (TDI) detector modified to receive alternate defocused images on alternate scanning rows. TDI detectors can be modified to acquire two images by blocking every other column, or by optical devices such as gratings or micro lens arrays that divert light onto alternate columns, and the frequency shifting of the detectors is synchronized with the relative motion between the optics and the photomask.

An example of a TDI array that collects two images is presented in FIG. 8B. Individual ones of opaque covering 807 blocks alternate array sensor elements 805. The TDI is a CCD array that integrates signals by shifting information (by shifting electrical charges) from one imaging sensor to the next at a shift frequency under the control of computer 109 of FIG. 1A in conjunction with the control of modulator 801. If the sensor is exposed to two images that alternate with the shift frequency, then the two images will be stored in an interleaved manner on the array. Thus by coordinating the modulation of the single illumination beam 111′ with the scanning of the TDI detector 804 so modified, both of the modulated, modified illumination beams 111T′ can be collected on a single imaging sensor. A seventh embodiment of the present invention is shown in FIG. 9 as a focus-based, projection-type inspection apparatus. The illumination system directs a pair of differently focused and polarized illumination beams 111′ (by means not shown) through the quarter-wave plate 701 and the focusing lens 703. Lines with arrows in FIG. 9 indicate the polarization orientation of the various light beams. The differently diverging, differently polarized beams can be produced, for example, using the birefringent lens 305 of the first embodiment. The collection system 107T′ includes focusing optics which includes specifically the birefringent objective 803, and a separation and imaging detector which includes the quarter-wave plate 707, a Wollaston prism 901, a focusing lens 903, and a standard TDI imaging detector 713. The birefringent objective 803 and Wollaston prism 901 work together to produce two side-by-side images of the illuminated photomask 103. Two-dimensional images are acquired on the TDI detector 713 of both modified illumination beams 111T' by scanning the photomask 103 in time with the TDI shift frequency. Analysis of the pairs of signals can be performed in data analysis system 125 or within the detector electronic or other devices that are configured to compare pairs of signals.

An eighth focus-based, projection-type embodiment is shown in FIG. 10. As in the seventh embodiment, a pair of differently focused and differently polarized illumination beams 111' are provided from an illumination system 105'. Arrows indicate the polarization orientation of the various beams. The collection system 107T' includes focusing optics 129, specifically the objective 705, and separation and imaging detector 131 including the quarter-wave plate 707, a focusing lens 1001, a polarizing beam splitter 1003, and a standard TDI imaging detector 905. In this embodiment, the focusing lens 1001 and polarizing beam splitter 1003 cooperate to image the two differently focused images side-by-side on TDI imaging detector 713. By timing scanning of the photomask 103 with the TDI shift frequency, the detector 713 can be used to collect two-dimensional images of both modified illumination beams 111T'.

A ninth embodiment of a focus-based, projection-type inspection apparatus is shown in FIG. 11A. The fifth embodiment uses a pair of differently polarized and differently focused coaxial illumination beams 111'. Illumination system 105 includes the quarter-wave plate 701 and the focusing lens 703 to produce two differently focused spots on photomask 103. Arrows indicate the polarization orientation of the various beams. The collection system 107T' includes a birefringent objective 803, the quarter-wave plate 707, the focusing lens 711, a birefringent micro prism array 1101, and a TDI detector 703. The birefringent objective 803 is positioned to bring the differently polarized and focused transmitted beams 111T' onto the same approximate position on imaging detector 713.

FIG. 11B shows a side view of an imaging system for producing interlaced images according to the embodiment of FIG. 11A. The transmitted modified beams 111T' are scanned into the plane of the figure and focused to the same approximate focal plane but have different polarizations. A 2:1 beam expansion prism 1103 directs the modified beams 111T' onto a birefringent micro prism array 1101 that includes an array of prisms having the same approximate spacing as sensors 805. The individual birefringent prisms are configured to split an incoming beam having two different polarities into two, side-by-side beams. The array 1101 thus receives the two differently polarized, modified illumination beams 111T' and produces two interlaced images to detector 713. As before, the scanning can be timed to the TDI shift frequency to produce a two-dimensional image of both modified beams 111T'. Also, as before, alternatively only one beam instead of multiple beams may be produced at any one time to sequentially inspect the photomask While the fifth through the ninth embodiments above are illustrated using a pair of differently focused and differently polarized illumination beams, it will be understood that these embodiments may be implemented using a single illumination beam that is focused with critical illumination or Kohler illumination. Such and other variations are within the scope of the invention.

Zernike-based Systems

Embodiments of the invention employing Zernike point spread functions use components that are largely similar to the ones used in focused-based systems described, except that in the case of Zernike-based systems, the sensitivity to phase objects is introduced by the different Zernike point spread functions of the pair(s) of beams, whereas in the case of focus-based systems, the sensitivity to phase objects is introduced by the different defocusing or focusing points of the pair(s) of beams. As in the case of focused-based systems, more than one pair of laterally separated beams having different Zernike point spread functions may be employed to speed up the inspection process, where the different Zernike point spread functions may be introduced prior to or after the interaction with the photomask 103.

Zernike-based systems use optics having Zernike point spread functions to convert photomask phase information into amplitude information that can be readily converted to signals using a light-sensitive detector. Prior art Zernike systems inspect phase objects with optical systems having a single Zernike point spread function. See, for example, Born and Wolf, *Principles of Optics,* Seventh (expanded) Edition, Margaret Farley-Born and Emil Wolf, 1999, page 472. The inventive inspection system illuminates or inspects a photomask with complementary +/−90 degree phase shifted Zernike point spread functions. The present invention has greatly increased sensitivity by inspecting with complementary point spread functions and combining the two resulting signals from corresponding photomask positions. In one embodiment the complementary Zernike point spread functions are generated with orthogonal polarizations, allowing for efficient separation into two complementary images or signals.

While complementary +/−90 degree phase shifted Zernike point spread functions are preferable, it will be understood that complementary +/−α degree phase shifted Zernike point spread functions may be used and is within the scope of the invention, where α is between the values of 0 and 180 degrees.

FIGS. 14A and 14B are schematics of a tenth embodiment of a scanning-type, Zernike-based inspection apparatus of the present invention. The tenth embodiment optical inspection system 101" for inspecting photomask 103 includes illumination system 105", transmitted light detection system 107T", and autofocus system 106 located within the illumination system. The illumination system 105" includes a laser or other appropriate source (not shown) to produce an illumination beam 300 that passes through the acousto-optic modulator 301 for focusing and scanning the beam, the lens 303 for collimating the beam, a Zernike phase plate 1401, the quarter-wave plate 313, and a Zernike objective 1403. Illumination system 105" of the tenth embodiment produces two illumination beams 111" having differing polarizations and Zernike point spread function, but that are substantially coaxial and have substantially the same approximate focal point 111-F". As with several of the previous embodiments, quarter-wave plate 313 causes the illumination beams near the photomask 103 to have circular polarizations. Polarization differences between the beams are reintroduced using a second, post-photomask quarter-wave plate, as described above.

The acousto-optic modulator 301 focuses and scans the beam, as indicated by the double-sided arrows. The photomask is moved by a stage 123 in the same manner as in the case of focus-based systems described above. The combination of the Zernike objective 1403 and the Zernike phase plate 1401 located at the back focal plane of the Zernike objective, at a distance L, produces, at focal point 111F", orthogonally polarized beams that have +/−90 degree complementary Zernike point spread functions. The construction of Zernike phase plate is specially designed to generate two coaxial beams of different polarizations and Zernike point spread functions, as discussed subsequently. Each of these beams interacts differently with the phase objects on photomask 103, allowing for inspection based on an analysis of the individual beams.

The two coincident illumination beams 111-1" and 111-2" are transmitted through, and modified by, the photomask 103, producing transmitted illumination beams 111-1T" and 111-2T". The transmitted light collection system 107T" separates the beams having complementary Zernike point spread functions according to their polarizations. The transmitted light collection system includes the collection lens 317, the quarter-wave plate 319 and TL detection system 1407T. The collection system 107T" collects the transmitted light, separates the beams by means of their polarizations, and generates signals proportional to each of the transmitted beams. Separation is accomplished by: 1) reintroducing the polarization difference between the two separately focused beams, and 2) passing the light through a polarizing beam splitter to spatially separate the beams. Specifically, the transmitted light collection system 107T includes the collection lens 317, the quarter-wave plate 319 and transmitted-light (TL) detection system 1407T that produces signals 111s". The TL detection system 1407T includes separation optics 119T" and detectors 121T". The lens 317 collects both of the modified beams 111T" and the quarter-wave plate 319 re-establishes a polarization difference in polarization between the two beams.

The polarization difference between the differently focused beams is used as the basis for separation of the beams in the TL detection system. The TL detection system 1407T is similar in construction in function to that of the first embodiment, and includes an aperture stop 325, a polarizing beam splitter 327, and two pairs of lenses and detectors: a first cylindrical lens 329 for focusing beam 111-2T" onto detector 331, and a second cylindrical lens 333 for focusing beam 111-1T" onto detector 335. The aperture stop 325, which has a pupil plane to limit the coherence to 0.5, transmits both of the modified beams 111T" before they are individually diverted according to their respective polarizations by the beam splitter 327. Both detectors 331 and 335 produce signals 111s" according to the intensity of beams 111-2T" and 111-1T", respectively.

Zernike phase plates according to the present invention are capable of producing orthogonal beams having complementary Zernike point spread functions. Examples of possible Zernike phase plates 1401, which are not meant to limit the present invention, are shown as a first implementation in FIGS. 15A and 15B, and as a second implementation in FIGS. 16A & 16B. The first implementation Zernike phase plate includes a fused quartz substrate 1501 and a crystalline quartz plate 1503. The crystalline quartz plate 1503 is birefringent and has surface relief to produce an extraordinary axis and ordinary axis that differ by 180 degrees, as shown by the arrows labeled "e" and "o," respectively. To produce the preferred +/−90 degree Zernike plate using a crystalline quartz plate 1503, the plate is of a thickness d given by $d=\lambda/(2(n_e-n_o))$. As noted above, a Zernike plate with complementary +/−α degree phase shifted Zernike point spread functions may also be used and is within the scope of the invention, where α is between the values of 0 and 180 degrees, such as one between about 70 to 110 degrees. Preferably, the Zernike plate includes a birefringent α-wave plate and a central region rotated by approximately 90 degrees, where α is between the values of 0 and 180 degrees, such as one between about 70 to 110 degrees, and preferably has the value of about 90 degrees.

The second implementation Zernike phase plate 1401 is a birefringent crystalline quartz quarter-wave plate that includes a first plate 1601 and a second plate 1603. The first and second plates 1601 and 1603 have ordinary and extraordinary axis that are reversed from one another, as shown in FIG. 16B. For a +/−90 degree Zernike plate, the thickness is given by: $d=\lambda/(4(n_e-n_o))=5.816\ \mu m$.

Individual Zernike illumination beams modified by the photomask 103 produce modified illumination beams 111-1T" and 111-2T" that are each sensitive to the amount of phase induced by the photomask. Combining indications of the two beam intensities by subtraction or through graphical methods, for example, provides a sensitive indication of phase objects, phase object errors, and/or classification of phase objects.

FIG. 17 is a schematic of an eleventh embodiment of a projector-type, Zernike-based inspection apparatus of the present invention, which illuminates the photomask 103 with one beam and images using Zernike optics that include elements that project two transmitted beams from the modified light. Specifically, by collecting modified light using a Zernike phase plate of the present invention located at the back focal plane of an objective, a pair of mutually orthogonal beams having different Zernike point spread functions is obtained. The photomask is moved by a stage 123 in the same manner as in the case of focus-based systems described above.

The eleventh embodiment inspection apparatus 101' includes the illumination system 105' and the transmitted light collection system 107T". The illumination system 105' includes a light source (not shown) that produces illumination beam 111', quarter-wave plate 701 and focusing lens 703. The illumination system 105' provides a focused illumination beams near photomask 103 positions that focus any amplitude objects that are present on the photomask. The transmitted light collection system 107T' includes the Zernike objective 1403, the quarter-wave plate 707, the Zernike phase plate 1401 located at the back focal plane of the Zernike objective, the Wollaston prism 901 for separating the transmitted beams 111T' according to their polarization (and thus their Zernike point spread function), the focusing lens 903, and the standard TDI imaging detector 713.

The embodiments above using Zernike plates may be modified to detect sequentially using a single radiation beam rather than simultaneously, and modified to detect reflected radiation rather than transmitted radiation, to arrive at embodiments substantially similar to those described above for the focus-based embodiments; such and other variations are within the scope of the invention. Focused-based embodiments such as those described in reference to FIGS. 8A, 8B, 11A, 11B may also be modified by replacing the birefringent lens of the focused-based systems by a polarization modulator; such and other variations are within the scope of the invention.

Data Analysis

The systems described above are configured to receive modified light from a photomask. In general, portions of the invention receive two modified light beams that are modified differently as a result of the modification by phase objects.

Specifically, the focus-based systems include light beams having different focuses and the Zernike-based system include light beams having different Zernike point spread functions. These systems all allow for extraction of phase information by comparison of pairs of signals from corresponding points on the photomask. Specifically, corresponding signals can be manipulated mathematically, as in a function of the two signals, or can be presented graphically, as in a plot of one signal against the other.

The correlation of sensor data with locations on the photomask would be obvious to one skilled in the art. Thus for example in FIG. 12, an array of photomask 103 areas is shown as a grid on the photomask. In several of the embodiment, two differently focused illumination beams are used to generate two corresponding images of the modified illumination beams, shown schematically as elements of array 1203 and 1205. Alternatively, a first image, shown schematically as array 1203 is collected, and an expected first image of the particular photomask, shown schematically as array 1205, is retrieved from a database. It is important that the image data be correlated to physical locations on the photomask 103, as indicated by the dashed line arrows.

Also shown in FIG. 12 is a subtraction analysis 1201 of the data, in which the two signal arrays 1203 and 1205 are subtracted from each other according to the corresponding physical location on the photomask 103 to form a difference array 1207. The object of analysis 1201 is to produce a map or image that can be used to relate data in difference array 1207 to phase defects. As noted previously, phase information may be obtained from differences between two differently focused images or differences in Zernike point spread function. As such it is understood that additional or different image processing steps may accomplish the objective of determining the location of phase defects. Thus the values or positions in the various arrays may be combined in various linear or non-linear transformations to highlight the detection of defects. Specifically, the values may be scaled or shifted, or the pair of values may be combined in other way than by pure subtraction. For example, the may be a calibration due to sensor element non-uniformities, or the values may be raised to some power before combining to accentuate the detection of phase defects or to minimize the effects of patterns on the photomask. In addition, adaptive techniques, such as neural networks, may be used to "train" an analysis system using known defects to recognize and/or classify defects. These techniques may involve using corresponding points or using data from neighboring photomask locations.

FIG. 13A shows an alternative graphical method 1301 of analyzing the data. The two signal arrays 1203 and 1205 are combined in a scatter plot 1303. Scatter plot 1303 is formed by extracting the two signals for each corresponding photomask location, and plotting the intensity of one signal on one axis and the intensity of the second signal on the other axis. Computer simulations have shown that scatter plots may be used for easy identification and/or classification of defects. Thus, as shown in FIG. 13B for example, 1303-a and 1303-b are scatter plots for different types of phase defects. Each of the plots has a main diagonal segment 1305. The diagonal segment corresponds to those photomask locations were the two signals are of equal strength.

Modeling results have shown that other features emerge depending on the type and location of the defect—in other words the other features can be used to classify the type of defect. For example, in scatter plot 1303-a, which corresponds to transmitted light through a phase altering divot within the center of a phase object, data 1307 forms an off-diagonal line near the end of diagonal 1305 heading towards the axis. In scatter plot 1303-b, which corresponds to transmitted light through a phase altering bump within the center of a phase object, data 1309 forms an off-diagonal line near the end of diagonal 1305 heading away from the axis. The position of the off-diagonal segments and angular orientation can be correlated to the position, size and orientation of the phase defect on the photomask. It is thus seen that scatter plot representations can be used to characterize and quantify the types of defects. In one embodiment, scatter plots are analyzed using image-processing techniques to categorize the images using calculations or measurements on known defects. In another embodiment, the scatter plots are analyzed using a neural network that is trained to correlate scatter plots with calculated or measured known defects.

A greater appreciation of the data analysis aspects of the present invention will be achieved by reference to FIG. 18. As previously discussed, FIG. 18 is an embodiment of the present invention for a focus-based optical system for inspecting a Levenson-type PSM 103, or photomask, with a phase defect 1801. FIG. 18B is a plot of the modified light intensity from the two modified or interacted beams 111-1T, such as two differently focused (defocused by $\pm\lambda/NA^2$) beams, or beams with different Zernike point spread functions; FIG. 18C is a scatter plot of the modified light intensities.

A comparison of the intensities of the two beams, taken from FIG. 18B, is shown in a graph 1813 of FIG. 18C. Specifically, graph 1813 is a scatter plot of the intensities of the two beams at corresponding points on the photomask 103. Light from the two illumination beams 111-1T and 111-2T that pass through the phase shifters 211 and 213 or is obstructed by the opaque regions 209 have approximately equal intensities, and fall along a diagonal line 1815. Light from the two illumination beams 111-1T and 111-2T that pass through or near the defect 1801 is modified differently and have different intensities. As a result the scatter plot of the defect modified beams falls on off-diagonal 1817. It has been found that the position, size and magnitude of defects can be characterized by the position, orientation and length of the off-diagonal line 1817 on an intensity scatter plot.

Additionally, the photomask phase information obtained by the present optical methods may be compared with acceptable, or allowed, and/or unacceptable, or forbidden, values, states, or differences between values or states. Thus photomask can be inspected by determining if the phase difference between adjoining phase shifters is one that is expected for a particular photomask design. Embodiment include but are not limited to inspecting all neighboring shifters to determine if the differences in phase shift are to be expected for a particular photomask.

It is to be understood that while the invention has been described above in conjunction with preferred specific embodiments, the description and examples are intended to illustrate and not limit the scope of the invention, which is defined by the scope of the appended claims and their equivalents. All documents referred to herein are incorporated by reference in their entireties.

What is claimed is:

1. An optical inspection apparatus for inspecting an article having a front surface and detecting optical variations therein, said apparatus comprising:

an optical system comprising an illumination system providing at least one illumination beam along an illumination path, where each illumination beam has an associated area on the front surface of the article, and where each illumination beam is associated with a focal plane of the optical system at a distance from the front surface; and a collection system producing at least two signals containing different phase information in response to said at least one illumination beam after modification by said article; and an analyzer determining said variations in the phase or amplitude of modified illumination beams at associated front surface area(s) according to said signals.

2. The optical inspection apparatus of claim 1, wherein said optical variations include amplitude objects, and wherein a focus of the optical system is such that the collection system produces two signals of approximately the same magnitude.

3. The optical inspection apparatus of claim 1, wherein the focal plane is associated with the illumination system.

4. The optical inspection apparatus of claim 1, wherein the focal plane is associated with the collection system.

5. The optical inspection apparatus of claim 1, wherein said at least one illumination beam is substantially monochromatic.

6. The optical inspection apparatus of claim 1, wherein said at least one illumination beam is nearly circularly polarized at said front surface area.

7. The optical inspection apparatus of claim 1, wherein at least one of said at least one illumination beam is modified by transmission through or reflection from said article.

8. The optical inspection apparatus of claim 1, wherein the collection system collects the at least two signals sequentially or substantially simultaneously.

9. The optical inspection apparatus of claim 1, further comprising a mechanism causing relative motion between the article and the optical system to scan said article, and wherein said analyzer generates positionally identified signals during the relative motion.

10. The optical inspection apparatus of claim 1, further comprising a mechanism changing a position of the focal plane relative to the article.

11. The optical inspection apparatus of claim 1, said illumination system providing at least one pair of illumination beams, wherein said analyzer compares signals from said at least one pair of modified illumination beams according to the associated front surface area, where each of the illumination beams in the at least one pair is associated with a focal plane of the optical system at a distance from the front surface.

12. The optical inspection apparatus of claim 1, wherein said analyzer determines said variations by subtracting the signals.

13. The optical inspection apparatus of claim 1, wherein said analyzer determines said variations by graphing the signals.

14. The optical inspection apparatus of claim 1, wherein said analyzer compares the signals to a threshold.

15. The optical inspection apparatus of claim 1, wherein said illumination system provides for scanning said at least one of said at least one illumination beam across said article.

16. The optical inspection apparatus of claim 1, wherein said optical inspection apparatus is a focus-based inspection apparatus, wherein said illumination system provides one or more pairs of illumination beams, wherein each pair of illumination beams comprises two illumination beams associated with two different focal planes, and wherein said collection system produces one or more pairs of signals in response to each pair of illumination beams modified by the article.

17. The optical inspection apparatus of claim 16, wherein said optical system has a numerical aperture NA, wherein at least one of said pairs of illumination beams is of substantially the same wavelength $\lambda$, and wherein a distance between the focal planes associated with such pair of illumination beams is less than or equal to $4\lambda/NA^2$.

18. The optical inspection apparatus of claim 16, wherein said optical inspection apparatus is a scanning-type inspection apparatus, said illumination system further comprising:

an illumination source providing at least one source beam; and difference-inducing optics producing at least one pair of divergent illumination beams in response to said at least one source beam.

19. The optical inspection apparatus of claim 18, wherein said source beam contains linearly polarized radiation, said difference-inducing optics comprising a birefringent lens having ordinary and extraordinary axes oriented approximately 45 degrees to the polarizations of said illumination beams such that the illumination beams of the at least one pair have orthogonal polarizations.

20. The optical inspection apparatus of claim 19, said collection system further comprising separation optics separating said at least one pair of polarized and reflected or transmitted illumination beams; and one or more detectors producing said signals from said separated beams.

21. The optical inspection apparatus of claim 20, wherein said separation optics comprises a polarization beam splitter separating said modified illumination beams by their polarizations.

22. The optical inspection apparatus of claim 18, said illumination source further comprising a light source providing said source beam, and a multiple beam producing element producing from said source beam said at least two or more pairs of illumination beams spatially separated from one another.

23. The optical inspection apparatus of claim 22, wherein said multiple beam producing element comprises a diffraction grating or a Fresnel zone plate.

24. The optical inspection apparatus of claim 22, said illumination system further comprising an objective focusing the two or more pairs of illumination beams to different associated front surface areas.

25. The optical inspection apparatus of claim 24, said collection system comprising two or more corresponding sets of detectors detecting the two or more modified illumination beams after modification of the beams by the article.

26. The optical inspection apparatus of claim 18, said difference-inducing optics comprising a multifocal zone plate.

27. The optical inspection apparatus of claim 26, said collection system further comprising a spatial filter to separate said modified illumination beams according to the focal distance.

28. The optical inspection apparatus of claim 18, said article transmitting and reflecting said at least one illumination beam, wherein said collection system comprises a first collection system producing signals in response to said at least one transmitted illumination beam, and a second collection system producing signals in response to said at least one reflected illumination beam.

29. The optical inspection apparatus of claim 1, wherein said optical inspection apparatus is a projector-type inspection apparatus, said illumination system further comprising:

an illumination source providing a source beam; and a polarization modulator modulating said source beam to provide a pair of illumination beams having different polarizations.

30. The optical inspection apparatus of claim 29, said collection system further comprising:
an objective lens to collect said illumination beams after modification by said article;
separation optics to divert said modified illumination beams according to their polarizations; and
an imaging detector to collect said diverted modified illumination beams.

31. The optical inspection apparatus of claim 30, said separation optics further comprising a Wollaston prism, and wherein said objective lens is a birefringent lens, and wherein said imaging detector detects said separated modified illumination beams side-by-side on said detector.

32. The optical inspection apparatus of claim 31, said separation optics further comprising a birefringent micro prism array, and wherein said imaging detector detects said separated modified illumination beams on alternating detector rows.

33. The optical inspection apparatus of claim 32, said imaging detector employing time-delayed integration, wherein said array diverts the beams onto alternate columns of the detectors, and charge shifting of the detectors is synchronized with the relative motion between the optics and the photomask.

34. The optical inspection apparatus of claim 31, said imaging detector employing time-delayed integration at a line rate, said illumination system further comprising a device electronically switching said modulator substantially at the line rate of the detector.

35. The optical inspection apparatus of claim 30, said separation optics further comprising a polarizing beam splitter, and wherein said imaging detector detects said separated modified illumination beams side-by-side on said detector.

36. The optical inspection apparatus of claim 1, wherein said optical inspection apparatus is a Zernike-based inspection apparatus, where said optical inspection apparatus comprises an objective lens and a Zernike plate at the back focal plane of said objective lens, where said Zernike plate has orthogonally polarized, complementary +/−α degree Zernike point spread functions, where α is between the values of 0 and 180 degrees.

37. The optical inspection apparatus of claim 36, wherein said at least one illumination beam is of substantially the same wavelength λ, wherein said Zernike plate comprises a non-birefringent outer portion and a birefringent inner portion having a thickness d, and having, for wavelength λ, an index of refraction n, an extraordinary index of refraction $n_e$ and an ordinary index of refraction $n_o$, and where said thickness d is given by:

$$d=\lambda/(2(n_e-n_o)).$$

38. The optical inspection apparatus of claim 37, wherein said at least one illumination beam is one illumination beam, wherein said optical inspection apparatus is a projector-type inspection apparatus, said illumination system further comprising:
an illumination source providing a source beam; and
illumination optics to accept said light and focus said illumination beam onto said article.

39. The optical inspection apparatus of claim 38, said collection system further comprising:
an objective lens to collect radiation from said source beam after modification by said article;
separation optics to divert said collected radiation into modified illumination beams according to the focal distance and associated front surface area; and
an imaging detector to collect said diverted modified illumination beams.

40. The optical inspection apparatus of claim 39, said illumination optics further comprising:
a first quarter-wave plate circularly polarizing said source beam before it reaches the article; and
said collection system further comprising a second quarter-wave plate polarizing said collected radiation.

41. The optical inspection apparatus of claim 40, said separation optics further comprising said Zernike plate, where said Zernike plate accepts said collected radiation and produces a pair of modified illumination beams that are orthogonally polarized and have been subjected to said complementary +/−90 degree Zernike point spread functions, and a Wollaston prism, where said Wollaston prism and said Zernike plate cooperate to spatially separate and focus said pair of modified illumination beams onto said imaging detector.

42. The optical inspection apparatus of claim 36, wherein said at least one illumination beam is of substantially the same wavelength λ, said Zernike plate comprises a quarter wave plate having a thickness d, and for wavelength λ, said Zernike plate having an index of refraction n, an extraordinary index of refraction $n_e$ and an ordinary index of refraction $n_o$, and wherein said thickness d is given by:

$$d=\lambda/(4(n_e-n_o)).$$

43. The optical inspection apparatus of claim 36, wherein said optical inspection apparatus is a scanning-type inspection apparatus, wherein said illumination system provides one pair of illumination beams, said illumination system further comprising:
an illumination source to provide a source beam;
said Zernike plate producing said pair of illumination beams in response to the source beam, where said pair of illumination beams are approximately coaxial, are substantially orthogonally polarized, and have substantially complementary +/−90 degree Zernike point spread functions; and
said objective lens accepting and focusing said pair of illumination beams.

44. The optical inspection apparatus of claim 43, wherein said Zernike plate comprises a non-birefringent substrate and a birefringent plate on said non-birefringent substrate.

45. The optical inspection apparatus of claim 43, wherein said Zernike plate comprises a birefringent α-wave plate and a central region rotated by approximately 90 degrees, where α is between the values of 0 and 180 degrees.

46. The optical inspection apparatus of claim 45, wherein α has a value between about 70 to 110 degrees.

47. The optical inspection apparatus of claim 43, wherein said one pair of modified illumination beam is a pair of transmitted or reflected illumination beams, said collection system further comprising:
at least one collection lens to collect said pair of transmitted or reflected illumination beams;
separation optics diverting individual ones of said pair of transmitted or reflected illumination beams according to their polarizations;
an aperture stop; and
one or more detectors for producing said signals from said diverted beams.

48. The optical inspection apparatus of claim 1, said illumination system further comprising a first quarter-wave plate converting the illumination beam(s) to circularly polarized beam(s), said collection system further comprising:

an objective collecting at least one pair of modified illumination beams;

a second quarter-wave plate converting said at least one pair of modified illumination beams collected by the objective to linearly polarized beams.

49. The optical inspection apparatus of claim 1, further comprising an autofocus optical system.

50. A method to determine optical variations of an article with an optical system according to the modification of light by the article having a front surface, said method comprising:

a) obtaining at least two signals containing different phase information from modification of at least one light beam by the article at the same approximate front surface location, where said at least one light beam is associated with different focal planes at distances from said front surface; and b) comparing said at least two signals to determine said optical variations in the article.

51. The method of claim 50, further comprising focusing two or more beams to different focal planes away from the front surface, wherein said obtaining comprises collecting light from the two or more beams after they are transmitted through or reflected by the article.

52. The method of claim 50, said at least one beam being transmitted or reflected by the article, further comprising collecting and focusing transmitted or reflected light from the at least one beam to detectors from two or more different focal planes away from the front surface, wherein said obtaining comprises providing the detectors which produce the signals in response to the collected and focused light.

53. The method of claim 50, wherein said obtaining comprises passing at least two light beams through plates having Zernike point spread functions, and wherein said light beams are modified by said optical variations according to the Zernike point spread functions of said corresponding light beam.

54. The method of claim 50, said article being a photomask, wherein said photomask has errors characterized by phase differences between locations on said mask, and wherein said errors are detected by comparing said at least two signals.

55. The method of claim 50, wherein said comparing comprises subtracting.

56. The method of claim 50, wherein said comparing comprises graphing.

57. The method of claim 50, wherein said comparing comprises a comparison with forbidden and allowed optical variations.

58. The method of claim 50, wherein said at least one beam is modified by being transmitted through said article.

59. The method of claim 50, wherein said at least one light beam is modified by being reflected from said article.

60. The method of claim 50, wherein said at least two signals are obtained substantially simultaneously.

61. The method of claim 50, wherein said at least two signals are obtained sequentially in time.

62. The method of claim 50, further comprising repeating steps a) and b) for a plurality of measurement locations.

63. The method of claim 50, further comprising collecting light from said at least one light beam and from individual points of the article, wherein said obtaining comprises obtaining at least two signals from such light at each of such points, and said method further comprising assembling an image of said article from said at least two signals from light collected at different points of the article.

64. An optical inspection method for inspecting a transparent substrate having a surface and detecting optical variations therein, said method comprising:

providing at least one illumination beam along an illumination path, where said at least one illumination beam has an associated area on the surface of the substrate; and producing substantially simultaneously at least two signals containing different phase information in response to said at least one illumination beam interacting with said substrate; and determining said variations in the phase or amplitude of modified illumination beams at associated surface area according to said signals.

65. The method of claim 64, said at least one illumination beam being transmitted or reflected by the article, said producing comprising imaging the transmitted or reflected illumination beam onto detectors to produce substantially simultaneously the at least two signals.

66. The method of claim 64, and where said at least one illumination beam is associated with a focal plane of an optical system to provide said at least one illumination beam or to produce substantially simultaneously the at least two signals, said focal plane located at a distance from the surface.

67. An optical inspection apparatus for inspecting an article having a front surface and detecting optical variations therein, said apparatus comprising:

an optical system comprising an illumination system providing at least one illumination beam along an illumination path, where each illumination beam has an associated area on the front surface of the article;

a collection system producing at least two signals containing different phase information in response to said at least one illumination beam after modification by said article; and an analyzer determining said variations in the phase or amplitude of modified illumination beams at associated front surface area(s) according to said signals, wherein said illumination system or collection system comprises a Zernike plate with orthogonally polarized, complementary +/−α degree Zernike point spread functions, where α is between the values of 0 and 180 degrees.

68. The optical inspection apparatus of claim 67, wherein the Zernike plate comprises a non-birefringent outer portion and a birefringent inner portion.

69. The optical inspection apparatus of claim 68, wherein said at least one illumination beam contains a component of wavelength λ, said birefringent inner portion having a thickness d, an extraordinary index of refraction $n_e$ and an ordinary index of refraction $n_o$ for wavelength λ, and where said thickness d is given by:

$$d=\lambda/(2(n_e-n_o)).$$

70. The optical inspection apparatus of claim 67, wherein said at least one illumination beam contains a component of wavelength λ, wherein said Zernike plate comprises a birefringent outer portion and a birefringent inner portion, each portion having a thickness d, and having an index of refraction n, an extraordinary index of refraction $n_e$ and an ordinary index of refraction $n_o$ for wavelength λ, and wherein said thickness d is given by:

$$d=\lambda/(4(n_e-n_o)).$$

71. The optical inspection apparatus of claim 67, further comprising an objective lens, where the Zernike plate is located substantially at the back focal plane of said objective lens.

72. The optical inspection apparatus of claim 71, wherein said optical inspection apparatus is a scanning-type inspection apparatus, said illumination system providing one pair of illumination beams, said illumination system further comprising:

an illumination source to provide a source beam;

said Zernike plate producing said pair of illumination beams in response to the source beam, where said pair of illumination beams are approximately coaxial, are substantially orthogonally polarized, and have substantially complementary +/−90 degree Zernike point spread functions; and said objective lens focusing said pair of illumination beams.

73. The optical inspection apparatus of claim 67, wherein said Zernike plate comprises a non-birefringent substrate and a birefringent plate on said non-birefringent substrate.

74. The optical inspection apparatus of claim 67, wherein said Zernike plate comprises a birefringent $\alpha$-wave plate and a central region rotated by approximately 90 degrees, where $\alpha$ is between the values of 0 and 180 degrees.

75. The optical inspection apparatus of claim 67, wherein $\alpha$ has a value between about 70 to 110 degrees.

76. The optical inspection apparatus of claim 67, wherein said collection system collects from the article a pair of transmitted or reflected illumination beams, said collection system further comprising:

at least one collection lens to collect said pair of transmitted or reflected illumination beams;

separation optics diverting individual ones of said pair of transmitted or reflected illumination beams according to their polarizations;

an aperture stop; and one or more detectors for producing said signals from said diverted beams.

77. The optical inspection apparatus of claim 67, wherein said optical inspection apparatus is a projector-type inspection apparatus, said illumination system further comprising:

an illumination source providing a source beam; and illumination optics focusing said source beam onto said article.

78. The optical inspection apparatus of claim 77, said collection system further comprising:

an objective lens to collect radiation from said source beam after modification by said article;

separation optics to divert said collected radiation into modified illumination beams; and an imaging detector to collect said diverted modified illumination beams.

79. The optical inspection apparatus of claim 78, said illumination optics further comprising:

a first quarter-wave plate circularly polarizing said source beam before it reaches the article; and said collection system further comprising a second quarter-wave plate polarizing said collected radiation.

80. The optical inspection apparatus of claim 79, said separation optics comprising said Zernike plate, where said Zernike plate accepts said collected radiation and produces a pair of modified illumination beams that are orthogonally polarized and have been subjected to said complementary Zernike point spread functions, said separation optics further comprising a Wollaston prism, where said Wollaston prism and said Zernike plate cooperate to spatially separate and focus said pair of modified illumination beams onto said imaging detector.

81. An optical inspection method for inspecting an article having a front surface and detecting optical variations therein, said method comprising:

providing at least one illumination beam along an illumination path, where each illumination beam has an associated area on the front surface of the article;

producing at least two signals containing different phase information in response to said at least one illumination beam after modification by said article; and determining said variations in the phase or amplitude of modified illumination beams at associated front surface area(s) according to said signals, wherein said providing or producing employs a Zernike plate with orthogonally polarized, complementary +/−$\alpha$ degree Zernike point spread functions, where $\alpha$ is between the values of 0 and 180 degrees.

82. The optical inspection method of claim 81, wherein said providing employs said Zernike plate to provide a pair of illumination beams in response to a source beam, where said pair of illumination beams are approximately coaxial, are substantially orthogonally polarized, and have substantially complementary +/−90 degree Zernike point spread functions.

83. The optical inspection method of claim 81, where in $\alpha$ has a value between about 70 to 110 degrees.

84. The optical inspection method of claim 81, wherein said producing comprises:

collecting radiation from the article:

diverting the collected radiation into a pair of transmitted or reflected illumination beams according to their polarizations; and detecting said diverted beams to produce said signals.

85. The optical inspection method of claim 84, said detecting comprising imaging said diverted beams to an imaging detector.

86. The optical inspection method of claim 85, said diverting comprising employing said Zernike plate to produce a pair of modified illumination beams that are orthogonally polarized and have been subjected to said complementary Zernike point spread functions in response to said collected radiation.

87. The optical inspection method of claim 86, said diverting further comprising employing a Wollaston prism and said Zernike plate to spatially separate and focus said pair of modified illumination beams onto said imaging detector.

88. The optical inspection method of claim 81, said providing further comprising circularly polarizing said illumination beam before it reaches the article; and said producing further comprising collecting and polarizing radiation from the article.

* * * * *